United States Patent
Shinde et al.

(10) Patent No.: US 9,386,774 B2
(45) Date of Patent: *Jul. 12, 2016

(54) APPLICATION OF MIXOTROPHIC CHLORELLA FOR THE IMPROVED YIELD AND QUALITY OF SOLANACEAE PLANTS

(71) Applicant: Heliae Development, LLC, Gilbert, AZ (US)

(72) Inventors: Sandip Shinde, Gilbert, AZ (US); Nicholas Donowitz, Shelburne, VT (US); Michael Clint Rohlfsen, Edina, MN (US)

(73) Assignee: Heliae Development, LLC, Gilbert, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/602,362

(22) Filed: Jan. 22, 2015

(65) Prior Publication Data

US 2016/0165897 A1 Jun. 16, 2016

Related U.S. Application Data

(60) Provisional application No. 62/092,703, filed on Dec. 16, 2014.

(51) Int. Cl.
| | |
|---|---|
| *C12N 1/12* | (2006.01) |
| *A01N 65/03* | (2009.01) |
| *A01G 33/00* | (2006.01) |
| *C12N 1/00* | (2006.01) |

(52) U.S. Cl.
CPC .............. *A01N 65/03* (2013.01); *A01G 33/00* (2013.01); *C12N 1/005* (2013.01); *C12N 1/12* (2013.01)

(58) Field of Classification Search
CPC ....... A01N 65/03; A01G 33/00; C12N 1/005; C12N 1/12
See application file for complete search history.

(56) References Cited

U.S. PATENT DOCUMENTS

| | | | |
|---|---|---|---|
| 3,444,647 A | 5/1969 | Takahashi | |
| 3,889,418 A | 6/1975 | Porter et al. | |
| 4,235,043 A | 11/1980 | Harasawa | |
| 4,551,164 A | 11/1985 | Tenzer | |
| 4,774,186 A | 9/1988 | Schaefer, Jr. | |
| 4,846,870 A | 7/1989 | Weltzien | |
| 4,919,702 A | 4/1990 | Weltzien | |
| 5,034,416 A | 7/1991 | Smith | |
| 5,130,242 A | 7/1992 | Barclay | |
| 6,083,293 A | 7/2000 | Bath | |
| 6,893,479 B2 | 5/2005 | Eswaran | |
| 7,030,061 B2 | 4/2006 | DeLaFuenteJimenez | |
| 7,892,311 B2 | 2/2011 | Briand | |
| 8,122,637 B2 | 2/2012 | Blotsky | |
| 8,133,920 B2 | 3/2012 | Johnson | |
| 8,241,868 B2 | 8/2012 | Higashiyama | |
| 8,367,372 B2 | 2/2013 | Calt, Jr. | |
| 8,563,839 B2 | 10/2013 | Scheer | |
| 8,614,165 B2 | 12/2013 | Goodwin | |
| 8,623,110 B2 | 1/2014 | Bevans | |
| 8,623,423 B2 | 1/2014 | Cook | |
| 2003/0068303 A1 | 4/2003 | Selvig | |
| 2004/0031302 A1 | 2/2004 | Eswaran | |
| 2004/0049062 A1 | 3/2004 | Bijl et al. | |
| 2005/0119127 A1 | 6/2005 | Cambri | |
| 2009/0266125 A1 | 10/2009 | Doan | |
| 2011/0142875 A1 | 6/2011 | Piccirilli | |
| 2011/0312023 A1 | 12/2011 | Chuu | |
| 2011/0314881 A1 | 12/2011 | Hatcher | |
| 2012/0094831 A1 | 4/2012 | Bartley | |
| 2012/0192605 A1 | 8/2012 | McSpaddenGardener | |
| 2012/0208254 A1 | 8/2012 | Smith | |
| 2012/0247164 A1 | 10/2012 | Dahms | |
| 2013/0102465 A1 | 4/2013 | Lovatt | |
| 2014/0002452 A1 | 1/2014 | Levin | |
| 2014/0011246 A1 | 1/2014 | Sims | |
| 2014/0024529 A1 | 1/2014 | Smith | |
| 2014/0026258 A1 | 1/2014 | Bettiol | |
| 2014/0090431 A1 | 4/2014 | Blotsky | |
| 2014/0298717 A1 | 10/2014 | Ayers | |

FOREIGN PATENT DOCUMENTS

| | | |
|---|---|---|
| CN | 1063413 C | 3/2001 |
| CN | 101352249 A | 1/2011 |
| CN | 102001895 A | 4/2011 |
| CN | 102153413 A | 8/2011 |
| CN | 102616932 A | 8/2012 |
| CN | 102060578 B | 7/2013 |
| CN | 103990155 A * | 8/2014 |

(Continued)

OTHER PUBLICATIONS

Abd El-Baky, et al., "Enhancing antioxidant availability in wheat grains from plants grown under seawater stress in response to microalgae extract treatments," J. Science Food Agriculture 90, 2010, pp. 299-303.

Agroplasma Inc., Ferticell Product Catalog, Http://agroplasmausa.com/product-catalog, accessed Oct. 28, 2013, 18 pages.

Andrews, 'Quantifying the Fertilizer Value of Algal Meal: An Evaluation of an Integrated Dairy-Anaerobic Digester-Algae Production Facility,' A Thesis submitted to Oregon State University in partial fulfillment of the requirements for the degree of Master of Science, May 10, 2013, 132 pages.

Aono, et al., "Effect of foliar application of fertilizer on the growth and quality of new shoot of tea plant," Chagyo Gijutsu Kenkyu 1982, 63, pp. 23-32.

(Continued)

*Primary Examiner* — Abigail Fisher
(74) *Attorney, Agent, or Firm* — Hahn Loeser & Parks, LLP

(57) ABSTRACT

Methods of improving the yield and quality of plants in the Solanaceae family by administering an effective amount of a mixotrophic *Chlorella* based liquid composition in low concentration and low frequency applications are disclosed. The administration may comprise soil or foliar applications of the composition.

30 Claims, No Drawings

(56) References Cited

FOREIGN PATENT DOCUMENTS

| EP | 0253035 A1 | | 1/1988 |
|---|---|---|---|
| GB | 1432039 A | * | 4/1976 |
| JP | 2001151586 A | | 5/2001 |
| KR | 2005091318 A | | 9/2005 |
| KR | 2007066461 A | | 6/2007 |
| KR | 1232284 B1 | | 5/2013 |
| KR | 1232288 B1 | | 5/2013 |
| RU | 2277522 C1 | | 10/2006 |
| WO | 2004085343 A1 | | 10/2004 |
| WO | 2007122264 A2 | | 11/2007 |
| WO | 2011060126 A2 | | 5/2011 |
| WO | 2012151382 A1 | | 11/2012 |
| WO | 2014015184 A1 | | 1/2014 |
| WO | 2014020187 A1 | | 2/2014 |
| WO | 2014074769 A2 | | 5/2014 |
| WO | 2014074769 A2 | | 5/2014 |

OTHER PUBLICATIONS

Babu, et al., "Effect of Kappaphycus alvarezii SLF treatment on Seed germination, Growth and Development of seedling in some Crop plants," J. Acad. Indus. Res. vol. 1(4) Sep. 2012, 10, pp. 186-195.

Choleva, et al., "Preliminary study of the green algae chlorells (Chlorella vulgaris) for control on the root-knot nematode (Meloidogyne arenaria) in tomato plants and ectoparasite Xiphinema indexin grape seedlings," Commun Agric Appl Biol Sci, v 70, n 4, 2005 pp. 915-927.

Dasgan, et al., "Use of Some Microorganisms as Bio-Fertilizers in Soilless Grown Squash for Saving Chemical Nutrients," Acta Horticulturae, Issue 927, 2010 pp. 155-162.

Flynn, "Production and Deployment of Photosynthetic Nitrogen-fixing Biofertilizers," International Erosion Control Association—Proceedings of Conference 37, 2006, pp. 69-78.

Harper Kimball et al, 'Cyanobacteria and cyanolichens: Can they enhance availability of essential minerals for higher plants?' Great Basin Naturalist, vol. 53, No. 1, 1993, pp. 59-72.

Holden Testing Report, "Evaluating Heliae Technology as a foliar applied treatment in Bell Peppers for Quality and Production," Nov. 22, 2014 20 pages.

Holden Testing Report, "Evaluating Heliae Technology as a foliar applied treatment in Strawberries for Quality and Production," Nov. 22, 2014, 20 pages.

Holden Testing Report, "Evaluating Heliae Technology as a foliar applied treatment in Tomatoes for Quality and Production," Nov. 22, 2014, 17 pages.

Holden Testing Report, "Evaluating Heliae Technology as a foliar treatment in a Nursery Environment for Early Plant Growth," Nov. 9, 2014, 23 pages.

Holden Testing Report, "Evaluating Heliae Technology as a foliar treatment in a Wine Grape Vineyard for Quality and Production," Nov. 22, 2014, 16 pages.

Holden Testing Report, "Evaluating Heliae Technology as a soil applied treatment in a Wine Grape Vineyard for Quality and Production," Nov. 22, 2014, 17 pages.

Holden Testing Report, "Evaluating Heliae Technology as a soil applied treatment in Bell Peppers for Quality and Productions," Nov. 22, 2014 23 pages.

Holden Testing Report, "Evaluating Heliae Technology as a soil applied treatment in Strawberries for Quality and Production," Nov. 22, 2014 17 pages.

Holden Testing Report, "Evaluating Heliae Technology as a soil applied treatment in Tomatoes for Quality and Production," Nov. 10, 2014, 16 pages.

Holden Testing Report, "Evaluating Heliae Technology as a soil drench treatment in a Nursery Environment for Early Plant Growth," Nov. 9, 2014, 23 pages.

Holden Testing Report, "Evaluating Heliae Technology in a Nursery Environment for Plant Germination," Nov. 9, 2014, 27 pages.

IFA, Fertilizers and Agriculture Quarterly Newsletter, May 2013, 12 pages.

Irrigation Research Foundation and BioFlora, Case Study Yellow Field Corn, http://www.bioflora.com/case-study-corn/, accessed Apr. 10, 2014, 2 pages.

Jha, et al., "Efficacy of new Inexpensive Cyanobacterial Biofertilizer including its Shelf Life," World J. of Micorbiology and Biotechnology, v22 n1, 2006, pp. 73-79.

Khan, et al., "Seaweed Extracts as Biostimulants of Plant Growth and Development," J. Plant Growth Regul., 2009, 28, pp. 386-399.

Leonian, "Effect of Auxins from Some Green Algae upon Phytophthora Cactorum," Botanical Gazette, v 97, n 4, Jun. 1936, pp. 854-859.

Mahdi, et al., "Bio-Fertilizers in Organic Agriculture," J. of Phytology 2010, 2(10), pp. 42-54.

Moniem, et al., "Effect of Green Alga Cells Extract as Foliar Spray on Vegetative Growth, Yield and Berries Quality of Superior Grapevines," American-Eurasian J. Agric. & Environ. Sci., 4 (4), 2008, pp. 427-433.

Moore, et al., "Novel Cytotoxins and Fungicides from Blue-Green-Algae and Marine Animals Possessing Algal Symbionts," Pure & Appl. Chem., v 61, n 3, 1989, pp. 521-524.

Prasad, et al., "Detection and Quantification of some Plant Growth regulators in a seaweed-based foliar spray employing a mass spectrometric technique sans chromatographic separation," J. of Agricultural and Food Chemistry, 2010, 58, pp. 4594-4601.

Rathore, et al., "Effect of Seaweed Extract on the Growth, Yield and Nutrient Uptake of Soybean (Glycine max) Under Rainfed Conditions," South African J. of Botany, 75, 2009, pp. 351-355.

Rehm, "Use of Banded Fertilizer for Corn Production," 2002, retrieved from http://www.extension.umn.edu/distribution/cropsystems/DC7425.html on Apr. 15, 2013, 9 pages.

Sears, "Production and Application of an Aircraft Spreadable, Cyanobacterial Based Biological Soil Crust Inoculant for Soil Fertilization, Soil Stabilization and Atmospheric CO2 Drawdown and Sequestration," US Statutory Invention Registration Jul. 3, 2012.

Shaaban, et al., "Green Microalgae Water Extract and Micronutrients Foliar Application as Promoters to Nutrient Balance and Growth of Wheat Plants," J. of American Science 2010, 6(9), pp. 631-636.

Shah, et al., "Seaweed Sap as an Alternative Liquid Fertilizer for Yield and Quality Improvement of Wheat," J.Plant Nutrition, 36, 2013, pp. 192-200.

Zodape, et al., "Effect of Kappaphycus alvarezii (Doty) Doty ex silva. extract on grain quality, yield and some yield components of wheat (Triticum aestivum L.)," International J. of Plant Production 3 (2) Apr. 2009, pp. 97-102.

Zodape, et al., "Effect of liquid seaweed fertilizer on yield and quality of okra (Abelmoschus esculentus L.)," J of Scientific & Industrial Research, v 67, Dec. 2008, pp. 1115-1117.

Zodape, et al., "Enhanced yield and nutritional quality in green gram (Phaseolus radiata L) treated with seaweed (Kappaphycus alvarezii) extract," J. of Scientific & Industrial Research, v 69, Jun. 2010, pp. 468-471.

Zodape, et al., "Foliar application of seaweed sap as biostimulant for enhancement of yield and quality of tomato (Lycopersicon esculentum Mill.)," J. of Scientific and Industrial Research, v 70, Mar. 2011, pp. 215-219.

Faheed et al., "Effect of Chlorella vulgaris as Bio-fertilizer on Growth Parameters and Metabolic Aspects of Lettuce Plant," Journal of Agriculture & Social Sciences, vol. 4, No. 4, 2008, p. 165-169.

Huang et al., Harvesting of Chlorell sp. using hollow fiber ultra filtration. Springer 2012; 1-6.

Sanger. Freezing and thawing cultured cells. Sanger. 2001; 1-2.
Himedia. Chlorella broth. HiMedia. 2011; 102.

Steve. Chile pepper seed germination and growing tips. ushotstuff. com 2011;1-8.

Childress C. Seed Soaking/presprouting tips & ideas! part 1. Green Been Connection. 2011;1-7.

(56) References Cited

OTHER PUBLICATIONS

Megharaj Mallavarpu; Healthy Levels of Soil Algae Lift Plant Growth; Fertility; Farming Ahead No. 120—Dec. 2001. p. 1.

Karin L. Hastings et al., Effect of microalgae application on soil algal species diversity, cation exchange capacity and organic matter after herbicide treatments; [version 1; referees: 1 approved, 1 not approved]; Integrated Life Sciences Research Complex at Global Organics, Goodyear, AZ, 85338, USA. First Published: Nov. 14, 2014, 3:281, Latest published: Nov. 14, 2014, 3:281. pp. 1-19.

Nikolov et al., In Vitro Antifungal Examination of Potassium Sorbate Towards Some Phytopathogens; Bulgarian Journal of Agricultural Sicence, 17 (No. 2) 2011, 191-194 Agricultural Academy.

Shakhashiri; Chemical of the Week, General Chemistry; www.scifun.org.

\* cited by examiner

APPLICATION OF MIXOTROPHIC CHLORELLA FOR THE IMPROVED YIELD AND QUALITY OF SOLANACEAE PLANTS

CROSS REFERENCE TO RELATED APPLICATIONS

This application claims the benefit of U.S. Provisional Application No. 62/092,703, filed Dec. 16, 2014, entitled Application of Mixotrophic *Chlorella* for the Improved Yield and Quality of Solanaceae Plants, the entire contents of which are hereby incorporated by reference herein.

BACKGROUND

Whether at a commercial or home garden scale, growers are constantly striving to optimize the yield and quality of a crop to ensure a high return on the investment made in every growth season. As the population increases and the demand for raw plant materials goes up for the food and renewable technologies markets, the importance of efficient agricultural production intensifies. The influence of the environment on a plant's health and production has resulted in a need for strategies during the growth season which allow the plants to compensate for the influence of the environment and maximize production. Addition of nutrients to the soil or application to the foliage has been proposed to promote yield and quality in certain plants. The effectiveness may attributable to the ingredients or the method of preparing the product. Increasing the effectiveness of a product may reduce the amount of the product needed and increase efficiency of the agricultural process. Therefore, there is a need in the art for methods of enhancing the yield and quality of a plant.

SUMMARY

In one non-limiting embodiment, a method of enhancing yield of a Solanaceae plant may comprise: administering a liquid composition treatment comprising a *Chlorella* culture in which the microalgae cell content of the culture consists essentially of whole pasteurized cells in a concentration in the range of 0.001-0.400% solids by weight to a Solanaceae plant in an amount effective to increase utilization in a population of such plants compared to a substantially identical population of untreated plants.

In some embodiments, the administration may comprise contacting foliage of the plants with an effective amount of the liquid composition. In some embodiments, the liquid composition may comprise a concentration in the range of 0.003-0.080% solids by weight of whole pasteurized *Chlorella* cells.

In some embodiments, the liquid composition may be administered at a rate in the range of 10-50 gallons/acre. In some embodiments, the liquid composition may be administered by spraying. In some embodiments, the liquid composition may be administered every 3-28 days. In some embodiments, the liquid composition may be administered every 4-10 days. In some embodiments, the liquid composition may be first administered 5-14 days after the plant emerges from the soil.

In some embodiments, the administration may comprise contacting soil in the immediate vicinity of the plants with an effective amount of the liquid composition. In some embodiments, the liquid composition may comprise a concentration in the range of 0.003-0.055% solids by weight of whole pasteurized *Chlorella* cells. In some embodiments, the liquid composition may comprise a concentration in the range of 0.040-0.360% solids by weight of whole pasteurized *Chlorella* cells.

In some embodiments, the liquid composition may be administered at a rate in the range of 50-150 gallons per acre. In some embodiments, the liquid composition may be administered to the soil by a low volume irrigation system. In some embodiments, the liquid composition may be administered to the soil by a soil drench application. In some embodiments, the liquid composition may be administered every 3-28 days. In some embodiments, the liquid composition may be administered every 4-10 days. In some embodiments, the liquid composition may be first administered 5-14 days after the plant emerges from the soil.

In some embodiments, the Solanaceae plant may comprise at least one selected from the group consisting of tomato and bell pepper plants. In some embodiments, the whole *Chlorella* cells may not be subjected to a drying process. In some embodiments, the liquid composition may further comprise stabilizing means suitable for plants. In some embodiments, the *Chlorella* cells are cultured in mixotrophic conditions. In some embodiments, the liquid composition may not contain an active ingredient for enhancing a characteristic of the plant other than the culture of whole *Chlorella* cells.

In some embodiments, the method may further comprise increasing at least one selected from the group consisting of marketable plant weight, marketable plant yield, and marketable fruit weight. In some embodiments, the utilization may be increased by at least 80% compared to a substantially identical population of untreated plants. In some embodiments, the marketable plant weight may be increased by at least 200% compared to a substantially identical population of untreated plants. In some embodiments, the marketable plant yield may be increased by at least 150% compared to a substantially identical population of untreated plants. In some embodiments, the marketable fruit weight may be increased by at least 10% compared to a substantially identical population of untreated plants.

In another non-limiting embodiment, a method of enhancing yield of a Solanaceae plant may comprise: providing a liquid composition treatment comprising a *Chlorella* culture in which the microalgae cell content of the culture consists essentially of whole pasteurized *Chlorella* cells in a concentration in the range of 5-30% solids by weight; diluting the liquid composition with water to a concentration in the range of 0.001-0.400% solids by weight of whole pasteurized *Chlorella* cells; and administering the liquid composition treatment to a Solanaceae plant in an amount effective to increase plant yield in a population of such plants compared to a substantially identical population of untreated plants.

DETAILED DESCRIPTION

The Solanaceae plant family includes a large number of agricultural crops, medicinal plants, spices, and ornamentals in it's over 2,500 species. Taxonomically classified in the Plantae kingdom, Tracheobionta (subkingdom), Spermatophyta (superdivision), Magnoliophyta (division), Manoliopsida (class), Asteridae (subclass), and Solanales (order), the Solanaceae family includes, but is not limited to, potatoes, tomatoes, eggplants, various peppers, tobacco, and petunias. Plants in the Solanaceae can be found on all the continents, excluding Antarctica, and thus have a widespread importance in agriculture across the globe.

Particularly important in the production of fruit from Solanaceae plants is the yield and quality of fruit, which may be quantified as the number, weight, color, firmness, ripeness, moisture, degree of insect infestation, degree of disease or rot, and degree of sunburn of the fruit. A method of treating a plant to directly improve the characteristics of the plant, or to indirectly enhance the chlorophyll level of the plant for photosynthetic capabilities and health of the plant's leaves, roots, and shoot to enable robust production of fruit is therefore valuable in increasing the efficiency of marketable production. Marketable and unmarketable designations may apply to both the plant and fruit, and may be defined differently based on the end use of the product, such as but not limited to, fresh market produce and processing for inclusion as an ingredient in a composition. The marketable determination may assess such qualities as, but not limited to, color, insect damage, blossom end rot, softness, and sunburn. The term total production may incorporate both marketable and unmarketable plants and fruit. The ratio of marketable plants or fruit to unmarketable plants or fruit may be referred to as utilization and expressed as a percentage. The utilization may be used as an indicator of the efficiency of the agricultural process as it shows the successful production of marketable plants or fruit, which will be obtain the highest financial return for the grower, whereas total production will not provide such an indication.

To achieve such improvements in yield and quality of Solanaceae plants, the inventors developed a method to treat such plants with a low concentration of a liquid microalgae based composition. The microalgae of the liquid composition comprise *Chlorella* sp. cultured in mixotrophic conditions, which comprises a culture medium primary comprised of water with trace nutrients (e.g., nitrates, phosphates, vitamins, metals found in BG-11 recipe (available from UTEX The Culture Collection of Algae at the University of Texas at Austin, Austin, Tex.)), light as an energy source for photosynthesis, organic carbon (e.g., acetate, acetic acid) as both an energy source and a source of carbon. In some embodiments, the culture media may comprise BG-11 media or a media derived from BG-11 culture media (e.g., in which additional component(s) are added to the media and/or one or more elements of the media is increased by 5%, 10%, 15%, 20%, 25%, 33%, 50%, or more over unmodified BG-11 media). In some embodiments, the *Chlorella* may be cultured in non-axenic mixotrophic conditions in the presence of contaminating organisms, such as but not limited to bacteria. Methods of culturing such microalgae in non-axenic mixotrophic conditions may be found in WO2014/074769A2 (Ganuza, et al.), hereby incorporated by reference.

By artificially controlling aspects of the *Chlorella* culturing process such as the organic carbon feed (e.g., acetic acid, acetate), oxygen levels, pH, and light, the culturing process differs from the culturing process that *Chlorella* experiences in nature. In addition to controlling various aspects of the culturing process, intervention by human operators or automated systems occurs during the non-axenic mixotrophic culturing of *Chlorella* through contamination control methods to prevent the *Chlorella* from being overrun and outcompeted by contaminating organisms (e.g., fungi, bacteria). Contamination control methods for microalgae cultures are known in the art and such suitable contamination control methods for non-axenic mixotrophic microalgae cultures are disclosed in WO2014/074769A2 (Ganuza, et al.), hereby incorporated by reference. By intervening in the microalgae culturing process, the impact of the contaminating microorganisms can be mitigated by suppressing the proliferation of containing organism populations and the effect on the microalgal cells (e.g., lysing, infection, death, clumping). Thus through artificial control of aspects of the culturing process and intervening in the culturing process with contamination control methods, the *Chlorella* culture produced as a whole and used in the described inventive compositions differs from the culture that results from a *Chlorella* culturing process that occurs in nature.

During the mixotrophic culturing process the *Chlorella* culture may also comprise cell debris and compounds excreted from the *Chlorella* cells into the culture medium. The output of the *Chlorella* mixotrophic culturing process provides the active ingredient for composition that is applied to plants for improving yield and quality without separate addition to or supplementation of the composition with other active ingredients not found in the mixotrophic *Chlorella* whole cells and accompanying culture medium from the mixotrophic culturing process such as, but not limited to: non-*Chlorella* microalgae cells, microalgae extracts, macroalgae, macroalgae extracts, liquid fertilizers, granular fertilizers, mineral complexes (e.g., calcium, sodium, zinc, manganese, cobalt, silicon), fungi, bacteria, nematodes, protozoa, digestate solids, chemicals (e.g., ethanolamine, borax, boric acid), humic acid, nitrogen and nitrogen derivatives, phosphorus rock, pesticides, herbicides, insecticides, enzymes, plant fiber (e.g., coconut fiber).

Mixotrophic *Chlorella* is the dominate microalgae species in the liquid composition. In some embodiments, the microalgae population of the liquid composition is substantially mixotrophic *Chlorella*. In some embodiments, mixotrophic or non-mixotrophic *Chlorella* comprises at least 90% of the microalgae population of the liquid composition. In some embodiments, mixotrophic or non-mixotrophic *Chlorella* comprises at least 91% of the microalgae population of the liquid composition. In some embodiments, mixotrophic or non-mixotrophic *Chlorella* comprises at least 92% of the microalgae population of the liquid composition. In some embodiments, mixotrophic or non-mixotrophic *Chlorella* comprises at least 93% of the microalgae population of the liquid composition. In some embodiments, mixotrophic or non-mixotrophic *Chlorella* comprises at least 94% of the microalgae population of the liquid composition. In some embodiments, mixotrophic or non-mixotrophic *Chlorella* comprises at least 95% of the microalgae population of the liquid composition. In some embodiments, mixotrophic or non-mixotrophic *Chlorella* comprises at least 96% of the microalgae population of the liquid composition. In some embodiments, mixotrophic or non-mixotrophic *Chlorella* comprises at least 97% of the microalgae population of the liquid composition. In some embodiments, mixotrophic or non-mixotrophic *Chlorella* comprises at least 98% of the microalgae population of the liquid composition. In some embodiments, mixotrophic or non-mixotrophic *Chlorella* comprises at least 99% of the microalgae population of the liquid composition. Liquid compositions having at least 99% of a *Chlorella* microalgae strain (e.g., at least 99.3%, at least 99.5%, or even at least 99.9%), such as mixotrophic *Chlorella*, can be considered to have a single algal species in the liquid composition. In one aspect, the liquid composition lacks any detectable amount of any other microalgae species. In another aspect, the liquid composition lacks any amount of any other microorganism in the liquid composition other than the desired *Chlorella* microalgae (e.g., bacteria) that is above 1% of the composition by weight.

While separate active ingredients are not added to or supplemented in the mixotrophic *Chlorella* based composition, the liquid composition comprising the mixotrophic *Chlorella* whole cells and accompanying constituents from the culturing medium and process (e.g., trace nutrients, residual organic carbon, bacteria, cell debris, cell excretions) may be stabilized by heating and cooling in a pasteurization process. As shown in the Examples, the inventors found that the active ingredients of the mixotrophic *Chlorella* based composition maintained effectiveness in improving plant yield and quality when applied to Solanaceae plants after being subjected to the heating and cooling of a pasteurization process.

In some embodiments, the composition may be heated to a temperature in the range of 50-70° C. In some embodiments, the composition may be heated to a temperature in the range of 55-65° C. In some embodiments, the composition may be heated to a temperature in the range of 58-62° C. In some embodiments, the composition may be heated to a temperature in the range of 50-60° C. In some embodiments, the composition may be heated to a temperature in the range of 60-70° C.

In some embodiments, the composition may be heated for a time period in the range of 90-150 minutes. In some embodiments, the composition may be heated for a time period in the range of 110-130 minutes. In some embodiments, the composition may be heated for a time period in the range of 90-100 minutes. In some embodiments, the composition may be heated for a time period in the range of 100-110 minutes. In some embodiments, the composition may be heated for a time period in the range of 110-120 minutes. In some embodiments, the composition may be heated for a time period in the range of 120-130 minutes. In some embodiments, the composition may be heated for a time period in the range of 130-140 minutes. In some embodiments, the composition may be heated for a time period in the range of 140-150 minutes.

In some embodiments, the composition may be cooled to a temperature in the range of 35-45° C. In some embodiments, the composition may be cooled to a temperature in the range of 36-44° C. In some embodiments, the composition may be cooled to a temperature in the range of 37-43° C. In some embodiments, the composition may be cooled to a temperature in the range of 38-42° C. In some embodiments, the composition may be cooled to a temperature in the range of 39-41° C.

In some embodiments, the mixotrophic *Chlorella* may be previously frozen and thawed before inclusion in the liquid composition. In some embodiments, the mixotrophic *Chlorella* may not have been subjected to a previous freezing or thawing process. In some embodiments, the mixotrophic *Chlorella* whole cells have not been subjected to a drying process. The cell walls of the mixotrophic *Chlorella* of the composition have not been lysed or disrupted, and the mixotrophic *Chlorella* cells have not been subjected to an extraction process or process that pulverizes the cells. The mixotrophic *Chlorella* whole cells are not subjected to a purification process for isolating the mixotrophic *Chlorella* whole cells from the accompanying constituents of the culturing process (e.g., trace nutrients, residual organic carbon, bacteria, cell debris, cell excretions), and thus the whole output from the mixotrophic *Chlorella* culturing process comprising whole *Chlorella* cells, culture medium, cell excretions, cell debris, bacteria, residual organic carbon, and trace nutrients, is used in the liquid composition for application to plants. In some embodiments, the mixotrophic *Chlorella* whole cells and the accompanying constituents of the culturing process are concentrated in the composition. In some embodiments, the mixotrophic *Chlorella* whole cells and the accompanying constituents of the culturing process are diluted in the composition to a low concentration. The mixotrophic *Chlorella* whole cells of the composition are not fossilized. In some embodiments, the mixotrophic *Chlorella* whole cells are not maintained in a viable state in the composition for continued growth after the method of using the composition in a soil or foliar application. In some embodiments, the mixotrophic *Chlorella* base composition may be biologically inactive after the composition is prepared. In some embodiments, the mixotrophic *Chlorella* base composition may be substantially biologically inactive after the composition is prepared. In some embodiments, the mixotrophic *Chlorella* base composition may increase in biological activity after the prepared composition is exposed to air.

In some embodiments, the composition may comprise 5-30% solids by weight of whole mixotrophic *Chlorella* cells. In some embodiments, the composition may comprise 5-20% solids by weight of whole mixotrophic *Chlorella* cells. In some embodiments, the composition may comprise 5-15% solids by weight of whole mixotrophic *Chlorella* cells. In some embodiments, the composition may comprise 5-10% solids by weight of whole mixotrophic *Chlorella* cells. In some embodiments, the composition may comprise 10-20% solids by weight of whole mixotrophic *Chlorella* cells. In some embodiments, the composition may comprise 10-20% solids by weight of whole mixotrophic *Chlorella* cells. In some embodiments, the composition may comprise 20-30% solids by weight of whole mixotrophic *Chlorella* cells. In some embodiments, further dilution of the whole mixotrophic *Chlorella* cells percent solids by weight may be occur before application for low concentration applications of the composition.

In some embodiments, the composition may comprise less than 1% solids by weight of whole mixotrophic *Chlorella* cells. In some embodiments, the composition may comprise less than 0.9% solids by weight of whole mixotrophic *Chlorella* cells. In some embodiments, the composition may comprise less than 0.8% solids by weight of whole mixotrophic *Chlorella* cells. In some embodiments, the composition may comprise less than 0.7% solids by weight of whole mixotrophic *Chlorella* cells. In some embodiments, the composition may comprise less than 0.6% solids by weight of whole mixotrophic *Chlorella* cells. In some embodiments, the composition may comprise less than 0.5% solids by weight of whole mixotrophic *Chlorella* cells. In some embodiments, the composition may comprise less than 0.4% solids by weight of whole mixotrophic *Chlorella* cells. In some embodiments, the composition may comprise less than 0.3% solids by weight of whole mixotrophic *Chlorella* cells. In some embodiments, the composition may comprise less than 0.2% solids by weight of whole mixotrophic *Chlorella* cells. In some embodiments, the composition may comprise less than 0.1% solids by weight of whole mixotrophic *Chlorella* cells.

In some embodiments, the liquid composition may comprise low concentrations of bacteria contributing to the solids percentage of the composition in addition to the whole mixotrophic *Chlorella* cells. Examples of bacteria found in non-axenic mixotrophic conditions may be found in WO2014/074769A2 (Ganuza, et al.), hereby incorporated by reference. A live bacteria count may be determined using methods known in the art such as plate counts, plates counts using Petrifilm available from 3M (St. Paul, Minn.), spectrophotometric (turbidimetric) measurements, visual comparison of turbidity with a known standard, direct cell counts under a microscope, cell mass determination, and measurement of cellular activity. Live bacteria counts in a non-axenic mixotrophic microalgae culture may range from $10^4$ to $10^9$ CFU/mL, and may depend on contamination control measures taken during the culturing of the microalgae. The level of bacteria in the composition may be determined by an aerobic plate count which quantifies aerobic colony forming units (CFU) in a designated volume. In some embodiments, the composition comprises an aerobic plate count of 40,000-400,000 CFU/mL. In some embodiments, the composition comprises an aerobic plate count of 40,000-100,000 CFU/mL. In some embodiments, the composition comprises an aerobic plate count of 100,000-200,000 CFU/mL. In some embodiments, the composition comprises an aerobic plate count of 200,000-300,000 CFU/mL. In some embodiments, the composition comprises an aerobic plate count of 300,000-400,000 CFU/mL.

In some embodiments, stabilizing means that are not active regarding the improvement of plant yield and quality, but instead aid in stabilizing the composition may be added to prevent the proliferation of unwanted microorganisms (e.g., yeast, mold) and prolong shelf life. Such inactive but stabilizing means may comprise an acid, such as but not limited to phosphoric acid, and a yeast and mold inhibitor, such as but not limited to potassium sorbate. In some embodiments, the stabilizing means are suitable for plants and do not inhibit the growth or health of the plant. In the alternative, the stabilizing means may contribute to nutritional properties of the liquid composition, such as but not limited to, the levels of nitrogen, phosphorus, or potassium.

In some embodiments, the composition may comprise less than 0.3% phosphoric acid. In some embodiments, the composition may comprise 0.01-0.3% phosphoric acid. In some embodiments, the composition may comprise 0.05-0.25% phosphoric acid. In some embodiments, the composition may comprise 0.01-0.1% phosphoric acid. In some embodiments, the composition may comprise 0.1-0.2% phosphoric acid. In some embodiments, the composition may comprise 0.2-0.3% phosphoric acid.

In some embodiments, the composition may comprise less than 0.5% potassium sorbate. In some embodiments, the composition may comprise 0.01-0.5% potassium sorbate. In some embodiments, the composition may comprise 0.05-0.4% potassium sorbate. In some embodiments, the composition may comprise 0.01-0.1% potassium sorbate. In some embodiments, the composition may comprise 0.1-0.2% potassium sorbate. In some embodiments, the composition may comprise 0.2-0.3% potassium sorbate. In some embodiments, the composition may comprise 0.3-0.4% potassium sorbate. In some embodiments, the composition may comprise 0.4-0.5% potassium sorbate.

The composition is a liquid and substantially comprises water. In some embodiments, the composition may comprise 70-95% water. In some embodiments, the composition may comprise 85-95% water. In some embodiments, the composition may comprise 70-75% water. In some embodiments, the composition may comprise 75-80% water. In some embodiments, the composition may comprise 80-85% water. In some embodiments, the composition may comprise 85-90% water. In some embodiments, the composition may comprise 90-95% water. The liquid nature and high water content of the composition facilitates administration of the composition in a variety of manners, such as but not limit to: flowing through an irrigation system, flowing through an above ground drip irrigation system, flowing through a buried drip irrigation system, flowing through a central pivot irrigation system, sprayers, sprinklers, and water cans.

The liquid composition may be used immediately after formulation, or may be stored in containers for later use. In some embodiments, the composition may be stored out of direct sunlight. In some embodiments, the composition may be refrigerated. In some embodiments, the composition may be stored at 1-10° C. In some embodiments, the composition may be stored at 1-3° C. In some embodiments, the composition may be stored at 3-5° C. In some embodiments, the composition may be stored at 5-8° C. In some embodiments, the composition may be stored at 8-10° C.

Administration of the liquid composition treatment to a Solanaceae plant may be in an amount effective to produce an enhanced characteristic in plants compared to a substantially identical population of untreated plants. Such enhanced characteristics may comprise increased plant yield, increased plant growth, increased plant quality, increased plant health, increased fruit yield, increased fruit growth, and increased fruit quality. Not limiting examples of such enhanced characteristics may comprise increased marketable plant weight, increased marketable plant yield, increased marketable fruit weight, increased production plant weight, increased production fruit weight, increased utilization (indicator of efficiency in the agricultural process based on ratio of marketable fruit to unmarketable fruit), increased chlorophyll content (indicator of plant health), increased plant weight (indicator of plant health), increased root weight (indicator of plant health), and increased shoot weight (indicator of plant health). Such enhanced characteristics may occur individually in a plant, or in combinations of multiple enhanced characteristics. Surprisingly, the inventors found that administration of the described composition in low concentration and low frequency applications was effective in producing enhanced characteristics in Solanaceae plants.

In some embodiments, the administration of the liquid composition may increase utilization by 80-100% compared to a substantially identical population of untreated plants. In some embodiments, administration of the liquid composition may increase utilization by at least 80% compared to a substantially identical population of untreated plants. In some embodiments, administration of the liquid composition may increase utilization by at least 85% compared to a substantially identical population of untreated plants. In some embodiments, administration of the liquid composition may increase utilization by at least 90% compared to a substantially identical population of untreated plants. In some embodiments, administration of the liquid composition may increase utilization by at least 95% compared to a substantially identical population of untreated plants.

In some embodiments, the administration of the liquid composition may increase marketable plant weight by 200-290% compared to a substantially identical population of untreated plants. In some embodiments, administration of the liquid composition may increase the marketable plant weight by at least 200% compared to a substantially identical population of untreated plants. In some embodiments, administration of the liquid composition may increase the marketable plant weight by at least 210% compared to a substantially identical population of untreated plants. In some embodiments, administration of the liquid composition may increase the marketable plant weight by at least 220% compared to a substantially identical population of untreated plants. In some embodiments administration of the liquid composition may increase the marketable plant weight by at least 230% compared to a substantially identical population of untreated plants. In some embodiments administration of the liquid composition may increase the marketable plant weight by at least 240% compared to a substantially identical population of untreated plants. In some embodiments, administration of the liquid composition may increase the marketable plant weight by at least 250% compared a substantially identical population of untreated plants. In some embodiments, administration of the liquid composition may increase the marketable plant weight by at least 260% compared to a substantially identical population of untreated plants. In some embodiments, administration of the liquid composition may increase the marketable plant weight by at least 270% compared to a substantially identical population of untreated plants. In some embodiments, administration of the liquid composition may increase the marketable plant weight by at least 280% compared to a substantially identical population of untreated plants.

In some embodiments, the administration of the liquid composition may increase marketable plant yield by 150-230% compared to a substantially identical population of untreated plants. In some embodiments, administration of the liquid composition may increase the marketable plant yield by at least 150% compared to a substantially identical population of untreated plants. In some embodiments, administration of the liquid composition may increase the marketable plant yield by at least 180% compared to a substantially identical population of untreated plants. In some embodiments, administration of the liquid composition may increase the marketable plant yield by at least 190% compared to a substantially identical population of untreated plants. In some embodiments, administration of the liquid composition may increase the marketable plant yield by at least 200% compared to a substantially identical population of untreated plants. In some embodiments, administration of the liquid composition may increase the marketable plant yield by at least 210% compared to a substantially identical population of untreated plants. In some embodiments, administration of the liquid composition may increase the marketable plant yield by at least 220% compared to a substantially identical population of untreated plants.

In some embodiments, the administration of the liquid composition may increase marketable fruit weight by 10-50% compared to a substantially identical population of untreated plants. In some embodiments, administration of liquid composition may increase the marketable fruit weight by at least 10% compared to a substantially identical population of untreated plants. In some embodiments, administration of liquid composition may increase the marketable fruit weight by at least 20% compared to a substantially identical population of untreated plants. In some embodiments, administration of liquid composition may increase the marketable fruit weight by at least 30% compared to a substantially identical population of untreated plants. In some embodiments, administration of liquid composition may increase the marketable fruit weight by at least 40% compared to a substantially identical population of untreated plants. In some embodiments, administration of liquid composition may increase the marketable fruit weight by at least 45% compared to a substantially identical population of untreated plants.

In some embodiments, the administration of the liquid composition may increase production plant weight by 70-120% compared to a substantially identical population of untreated plants. In some embodiments, administration of liquid composition may increase production plant weight by at least 70% compared to a substantially identical population of untreated plants. In some embodiments, administration of liquid composition may increase the production plant weight by at least 80% compared to a substantially identical population of untreated plants. In some embodiments, administration of liquid composition may increase the production plant weight by at least 90% compared to a substantially identical population of untreated plants. In some embodiments, administration of liquid composition may increase the production plant weight by at least 100% compared to a substantially identical population of untreated plants. In some embodiments, administration of liquid composition may increase the production plant weight by at least 110% compared to a substantially identical population of untreated plants.

In some embodiments, the administration of the liquid composition may increase production fruit weight by 70-110% compared to a substantially identical population of untreated plants. In some embodiments, administration of liquid composition may increase production fruit weight by at least 70% compared to a substantially identical population of untreated plants. In some embodiments, administration of liquid composition may increase the production fruit weight by at least 80% compared to a substantially identical population of untreated plants. In some embodiments, administration of liquid composition may increase the production fruit weight by at least 90% compared to a substantially identical population of untreated plants. In some embodiments, administration of liquid composition may increase the production fruit weight by at least 100% compared to a substantially identical population of untreated plants. In some embodiments, administration of liquid composition may increase the production fruit weight by at least 105% compared to a substantially identical population of untreated plants.

In some embodiments, the administration of the liquid composition may increase the chlorophyll content by 15-40% compared to a substantially identical population of untreated plants. In some embodiments, administration of the liquid composition may increase the chlorophyll content by at least 15% compared to a substantially identical population of untreated plants. In some embodiments, administration of the liquid composition may increase the chlorophyll content by at least 20% compared to a substantially identical population of untreated plants. In some embodiments, administration of the liquid composition may increase the chlorophyll content by at least 25% compared to a substantially identical population of untreated plants. In some embodiments, administration of the liquid composition may increase the chlorophyll content by at least 30% compared to a substantially identical population of untreated plants.

In some embodiments, the administration of the liquid composition may increase the whole plant weight by 30-60% compared to a substantially identical population of untreated plants. In some embodiments, administration of the liquid composition may increase the whole plant weight by at least 30% compared to a substantially identical population of untreated plants. In some embodiments, administration of the liquid composition may increase the whole plant weight by at least 35% compared to a substantially identical population of untreated plants. In some embodiments, administration of the liquid composition may increase the whole plant weight by at least 40% compared to a substantially identical population of untreated plants. In some embodiments, administration of the liquid composition may increase the whole plant weight by at least 45% compared to a substantially identical population of untreated plants. In some embodiments, administration of the liquid composition may increase the whole plant weight by at least 50% compared to a substantially identical population of untreated plants. In some embodiments, administration of the liquid composition may increase the whole plant weight by at least 55% compared to a substantially identical population of untreated plants.

In some embodiments, the administration of the liquid composition may increase the root weight by 30-60% compared to a substantially identical population of untreated plants. In some embodiments, administration of the liquid composition may increase the root weight by at least 30% compared to a substantially identical population of untreated plants. In some embodiments, administration of the liquid composition may increase the root weight by at least 35% compared to a substantially identical population of untreated plants. In some embodiments, administration of the liquid composition may increase the root weight by at least 40% compared to a substantially identical population of untreated plants. In some embodiments, administration of the liquid composition may increase the root weight by at least 45% compared to a substantially identical population of untreated plants. In some embodiments, administration of the liquid composition may increase the root weight by at least 50% compared to a substantially identical population of untreated plants.

In some embodiments, the administration of the liquid composition may increase the shoot weight by 30-70% compared to a substantially identical population of untreated plants. In some embodiments, administration of the liquid composition may increase the shoot weight by at least 30% compared to a substantially identical population of untreated plants. In some embodiments, administration of the liquid composition may increase the shoot weight by at least 35% compared to a substantially identical population of untreated plants. In some embodiments, administration of the liquid composition may increase the shoot weight by at least 40% compared to a substantially identical population of untreated plants. In some embodiments, administration of the liquid composition may increase the shoot weight by at least 45% compared to a substantially identical population of untreated plants. In some embodiments, administration of the liquid composition may increase the shoot weight by at least 50% compared a substantially identical population of untreated plants. In some embodiments, administration of the liquid composition may increase the shoot weight by at least 55% compared to a substantially identical population of untreated plants. In some embodiments, administration of the liquid composition may increase the shoot weight by at least 60% compared to a substantially identical population of untreated plants.

Foliar Application

In one non-limiting embodiment, the administration of the liquid composition treatment may comprise contacting the foliage of the plant with an effective amount of the liquid composition. In some embodiments, the liquid composition may be sprayed on the foliage by a hand sprayer, a sprayer on an agriculture implement, or a sprinkler.

The composition may be diluted to a lower concentration for an effective amount in a foliar application by mixing a volume of the composition in a volume of water. The percent solids of mixotrophic *Chlorella* whole cells resulting in the diluted composition may be calculated by the multiplying the original percent solids in the composition by the ratio of the volume of the composition to the volume of water. In some embodiments, the effective amount in a foliar application of the liquid composition may comprise a concentration in the range of 2-10 mL/gallon, resulting in a reduction of the percent solids of mixotrophic *Chlorella* whole cells from 5-30% to 0.002642-0.079252% (e.g., about 0.003% to about 0.080%). In some embodiments, the effective amount in a foliar application of the liquid composition may comprise a concentration in the range of 2-3 mL/gallon, resulting in a reduction of the percent solids of mixotrophic *Chlorella* whole cells from 5-30% to 0.002642-0.023775% (e.g., about 0.003% to about 0.025%). In some embodiments, the effective amount in a foliar application of the liquid composition may comprise a concentration in the range of 3-4 mL/gallon, resulting in a reduction of the percent solids of mixotrophic *Chlorella* whole cells from 5-30% to 0.003963-0.031701% (e.g., about 0.004% to about 0.035%). In some embodiments, the effective amount in a foliar application of the liquid composition may comprise a concentration in the range of 4-5 mL/gallon, resulting in a reduction of the percent solids of mixotrophic *Chlorella* whole cells from 5-30% to 0.005283-0.039626% (e.g., about 0.005% to about 0.040%). In some embodiments, the effective amount in a foliar application of the liquid composition may comprise a concentration in the range of 5-6 mL/gallon, resulting in a reduction of the percent solids of mixotrophic *Chlorella* whole cells from 5-30% to 0.006604-0.047551% (e.g., about 0.007% to about 0.050%). In some embodiments, the effective amount in a foliar application of the liquid composition may comprise a concentration in the range of 6-7 mL/gallon, resulting in a reduction of the percent solids of mixotrophic *Chlorella* whole cells from 5-30% to 0.007925-0.055476% (e.g., about 0.008% to about 0.055%). In some embodiments, the effective amount in a foliar application of the liquid composition may comprise a concentration in the range of 7-8 mL/gallon, resulting in a reduction of the percent solids of mixotrophic *Chlorella* whole cells from 5-30% to 0.009246-0.063401% (e.g., about 0.009% to about 0.065%). In some embodiments, the effective amount in a foliar application of the liquid composition may comprise a concentration in the range of 8-9 mL/gallon, resulting in a reduction of the percent solids of mixotrophic *Chlorella* whole cells from 5-30% to 0.010567-0.071327% (e.g., about 0.010% to about 0.070%). In some embodiments, the effective amount in a foliar application of the liquid composition may comprise a concentration in the range of 9-10 mL/gallon, resulting in a reduction of the percent solids of mixotrophic *Chlorella* whole cells from 5-30% to 0.011888-0.079252% (e.g., about 0.012% to about 0.080%).

The rate of application of the composition at the desired concentration may be expressed as a volume per area. In some embodiments, the rate of application of the liquid composition in a foliar application may comprise a rate in the range of 10-50 gallons/acre. In some embodiments, the rate of application of the liquid composition in a foliar application may comprise a rate in the range of 10-15 gallons/acre. In some embodiments, the rate of application of the liquid composition in a foliar application may comprise a rate in the range of 15-20 gallons/acre. In some embodiments, the rate of application of the liquid composition in a foliar application may comprise a rate in the range of 20-25 gallons/acre. In some embodiments, the rate of application of the liquid composition in a foliar application may comprise a rate in the range of 25-30 gallons/acre. In some embodiments, the rate of application of the liquid composition in a foliar application may comprise a rate in the range of 30-35 gallons/acre. In some embodiments, the rate of application of the liquid composition in a foliar application may comprise a rate in the range of 35-40 gallons/acre. In some embodiments, the rate of application of the liquid composition in a foliar application may comprise a rate in the range of 40-45 gallons/acre. In some embodiments, the rate of application of the liquid composition in a foliar application may comprise a rate in the range of 45-50 gallons/acre.

The frequency of the application of the composition may be expressed as the number of applications per period of time (e.g., two applications per month), or by the period of time between applications (e.g., one application every 21 days). In some embodiments, the plant may be contacted by the liquid composition in a foliar application every 3-28 days. In some embodiments, the plant may be contacted by the liquid composition in a foliar application every 4-10 days. In some embodiments, the plant may be contacted by the liquid composition in a foliar application every 18-24 days. In some embodiments, the plant may be contacted by the liquid composition in a foliar application every 3-7 days. In some embodiments, the plant may be contacted by the liquid composition in a foliar application every 7-14 days. In some embodiments, the plant may be contacted by the liquid composition in a foliar application every 14-21 days. In some embodiments, the plant may be contacted by the liquid composition in a foliar application every 21-28 days.

Foliar application(s) of the composition generally begin after the plant has become established, but may begin before establishment, at defined time period after planting, or at a defined time period after emergence form the soil in some embodiments. In some embodiments, the plant may be first contacted by the liquid composition in a foliar application 5-14 days after the plant emerges from the soil. In some embodiments, the plant may be first contacted by the liquid composition in a foliar application 5-7 days after the plant emerges from the soil. In some embodiments, the plant may be first contacted by the liquid composition in a foliar application 7-10 days after the plant emerges from the soil. In some embodiments, the plant may be first contacted by the liquid composition in a foliar application 10-12 days after the plant emerges from the soil. In some embodiments, the plant may be first contacted by the liquid composition in a foliar application 12-14 days after the plant emerges from the soil.

Soil Application

In another non-limiting embodiment, the administration of the liquid composition treatment may comprise contacting the soil in the immediate vicinity of the plant with an effective amount of the liquid composition. In some embodiments, the liquid composition may be supplied to the soil by injection into to a low volume irrigation system, such as but not limited to a drip irrigation system supplying water beneath the soil through perforated conduits or at the soil level by fluid conduits hanging above the ground or protruding from the ground. In some embodiments, the liquid composition may be supplied to the soil by a soil drench method wherein the liquid composition is poured on the soil.

The composition may be diluted to a lower concentration for an effective amount in a soil application by mixing a volume of the composition in a volume of water. The percent solids of mixotrophic *Chlorella* whole cells resulting in the diluted composition may be calculated by the multiplying the original percent solids of mixotrophic *Chlorella* whole cells in the composition by the ratio of the volume of the composition to the volume of water. In some embodiments, the effective amount in a soil application of the liquid composition may comprise a concentration in the range of 1-50 mL/gallon, resulting in a reduction of the percent solids of mixotrophic *Chlorella* whole cells from 5-30% to 0.001321-0.396258% (e.g., about 0.001% to about 0.400%). In some embodiments, the effective amount in a soil application of the liquid composition may comprise a concentration in the range of 1-10 mL/gallon, resulting in a reduction of the percent solids of mixotrophic *Chlorella* whole cells from 5-30% to 0.001321-0.079252% (e.g., about 0.001% to about 0.080%). In some embodiments, the effective amount in a soil application of the liquid composition may comprise a concentration in the range of 2-7 mL/gallon, resulting in a reduction of the percent solids of mixotrophic *Chlorella* whole cells from 5-30% to 0.002642-0.055476% (e.g., about 0.003% to about 0.055%). In some embodiments, the effective amount in a soil application of the liquid composition may comprise a concentration in the range of 10-20 mL/gallon, resulting in a reduction of the percent solids of mixotrophic *Chlorella* whole cells from 5-30% to 0.013201-0.158503% (e.g., about 0.013% to about 0.160%). In some embodiments, the effective amount in a soil application of the liquid composition may comprise a concentration in the range of 20-30 mL/gallon, resulting in a reduction of the percent solids of mixotrophic *Chlorella* whole cells from 5-30% to 0.026417-0.237755% (e.g., about 0.025% to about 0.250%). In some embodiments, the effective amount in a soil application of the liquid composition may comprise a concentration in the range of 30-45 mL/gallon, resulting in a reduction of the percent solids of mixotrophic *Chlorella* whole cells from 5-30% to 0.039626-0.356631% (e.g., about 0.040% to about 0.360%). In some embodiments, the effective amount in a soil application of the liquid composition may comprise a concentration in the range of 30-40 mL/gallon, resulting in a reduction of the percent solids of mixotrophic *Chlorella* whole cells from 5-30% to 0.039626-0.317007% (e.g., about 0.040% to about 0.320%). In some embodiments, the effective amount in a soil application of the liquid composition may comprise a concentration in the range of 40-50 mL/gallon, resulting in a reduction of the percent solids of mixotrophic *Chlorella* whole cells from 5-30% to 0.052834-0.396258% (e.g., about 0.055% to about 0.400%).

The rate of application of the composition at the desired concentration may be expressed as a volume per area. In some embodiments, the rate of application of the liquid composition in a soil application may comprise a rate in the range of 50-150 gallons/acre. In some embodiments, the rate of application of the liquid composition in a soil application may comprise a rate in the range of 75-125 gallons/acre. In some embodiments, the rate of application of the liquid composition in a soil application may comprise a rate in the range of 50-75 gallons/acre. In some embodiments, the rate of application of the liquid composition in a soil application may comprise a rate in the range of 75-100 gallons/acre. In some embodiments, the rate of application of the liquid composition in a soil application may comprise a rate in the range of 100-125 gallons/acre. In some embodiments, the rate of application of the liquid composition in a soil application may comprise a rate in the range of 125-150 gallons/acre.

The frequency of the application of the composition may be expressed as the number of applications per period of time (e.g., two applications per month), or by the period of time between applications (e.g., one application every 21 days). In some embodiments, the plant may be contacted by the liquid composition in a soil application every 3-28 days. In some embodiments, the plant may be contacted by the liquid composition in a soil application every 4-10 days. In some embodiments, the plant may be contacted by the liquid composition in a soil application every 18-24 days. In some embodiments, the plant may be contacted by the liquid composition in a soil application every 3-7 days. In some embodiments, the plant may be contacted by the liquid composition in a soil application every 7-14 days. In some embodiments, the plant may be contacted by the liquid composition in a soil application every 14-21 days. In some embodiments, the plant may be contacted by the liquid composition in a soil application every 21-28 days.

Soil application(s) of the composition generally begin after the plant has become established, but may begin before establishment, at defined time period after planting, or at a defined time period after emergence form the soil in some embodiments. In some embodiments, the plant may be first contacted by the liquid composition in a soil application 5-14 days after the plant emerges from the soil. In some embodiments, the plant may be first contacted by the liquid composition in a soil application 5-7 days after the plant emerges from the soil. In some embodiments, the plant may be first contacted by the liquid composition in a soil application 7-10 days after the plant emerges from the soil. In some embodiments, the plant may be first contacted by the liquid composition in a soil application 10-12 days after the plant emerges from the soil. In some embodiments, the plant may be first contacted by the liquid composition in a soil application 12-14 days after the plant emerges from the soil.

Whether in a soil or foliar application the method of use comprises relatively low concentrations of the liquid composition. Even at such low concentrations, the described composition has been shown to be effective at producing an enhanced characteristic in Solanaceae plants. The ability to use low concentrations allows for a reduced impact on the environment that may result from over application and an increased efficiency in the method of use of the liquid composition by requiring a small amount of material to produce the desired effect. In some embodiments, the use of the liquid composition with a low volume irrigation system in soil applications allows the low concentration of the liquid composition to remain effective and not be diluted to a point where the composition is no longer in at a concentration capable of producing the desired effect on the plants while also increasing the grower's water use efficiency. The ability to use low concentrations of mixotrophic *Chlorella* whole cells and lack of purification processes to isolate the cells also reduces the dewatering and processing needs of the microalgae which may be produced at low concentrations in the culturing stage, and thus increasing the energy efficiency in the method of preparing the product.

In conjunction with the low concentrations of mixotrophic *Chlorella* whole cells solids in the liquid composition necessary to be effective for enhancing the described characteristics of plants, the liquid composition may does not have be to administered continuously or at a high frequency (e.g., multiple times per day, daily). The ability of the liquid composition to be effective at low concentrations and a low frequency of application was an unexpected result, due to the traditional thinking that as the concentration of active ingredients decreases the frequency of application should increase to provide adequate amounts of the active ingredients. Effectiveness at low concentration and application frequency increases the material usage efficiency of the method of using the liquid composition while also increasing the yield efficiency of the agricultural process. The use of mixotrophic *Chlorella* whole cells that have not been previously subjected to processing to dry, extract, lyse, or otherwise disrupt the cell wall also increases energy efficiency in the method of preparing the product and allows the product to be produced in a quicker time frame.

EXAMPLES

Embodiments of the invention are exemplified and additional embodiments are disclosed in further detail in the following Examples, which are not in any way intended to limit the scope of any aspect of the invention described herein.

Example 1

An experiment was conducted to determine if a low concentration and low frequency application of a mixotrophic *Chlorella* based composition to bell pepper plants by soil application affected the yield of the plants. Bell pepper (*Capsicum annuum*) are part of the Solanaceae plant family and seeds were planted in a field in Ventura County, Calif. Two treatments were compared to an untreated control (UTC) and are listed in Table 1. A commercially available macroalgae extract based product was obtained from Acadian Seaplants Limited (30 Brown Avenue, Dartmouth, Nova Scotia, Canada, B3B 1X8) for comparison.

TABLE 1

| Treatment No. | Treatment Description |
|---|---|
| 1 | UTC - untreated water check |
| 2 | Mixotrophic *Chlorella* sp. - Whole Cells |
| 3 | Grower Standard Product - Acadian Liquid Seaweed Concentrate |

The mixotrophic *Chlorella* based composition was pasteurized, normalized to 10% solids, and stabilized with phosphoric acid ($H_3PO_4$) and potassium sorbate ($C_6H_7KO_2$), with the remaining balance consisting of water. The mixotrophic *Chlorella* whole cells were not previously subjected to a purification process to isolate the cells from the microalgae culturing medium, nor were the cells previously subjected to a drying, extraction, or other process that may lyse or disrupt the cell walls. The mixotrophic *Chlorella* composition was previously frozen and thawed, and was incorporated into the liquid composition for treatments used in this experiment after cold storage following being harvested from the microalgae culturing system. The composition comprising mixotrophic *Chlorella* used in the treatments of this experiment were not analyzed to quantify bacteria in the compositions, however aerobic plate counts for previous compositions prepared with the same components in the same manner contained 40,000-400,000 CFU/mL.

The mixotrophic *Chlorella* based composition was applied at a low concentration of 37.85 mL/gallon. The tested concentration of 37.85 mL/gallon diluted the composition which originally contained 10% solids by weight of mixotrophic *Chlorella* whole cells to the low percent solids content of only 0.099989%. The Acadian treatment was applied at a concentration of 18.9 mL/gallon. Five total treatments were applied at a low frequency (i.e., averaging about 20 days between applications), starting three weeks after plant establishment. The treatments occurred with 20 days between the first and second, 24 days between the second and third, 11 days between the third and fourth, and 26 days between the fourth and fifth. The low concentration and low frequency treatments were applied by injection into a low volume irrigation drip system supplying water at a rate of 100 gallons/acre using a Hypro pump operating at 25 psi.

The experiment was set up as a block designed study of eight replicates consisting of 30 seeds each. Visual observations were used to evaluate plant vigor on a scale of 0-5, with 0 corresponding to plant death and 5 corresponding to complete health. Production was evaluated by quality in the two categories of marketable and unmarketable. Unmarketable fruit was considered fruit which had heavy insect damage, blossom end rot, softness, and/or heavy sunburn. The field used in the experiment was growing bell peppers for processing, and thus the quality needed for fresh market produce was not the target achievement. Additionally, the bell peppers were left in the field a length of time to ensure the maximum amount of reddening before harvest for processing. The chlorophyll content was estimated by an SPAD value (Soil-Plant Analysis Development), a numeric value provided by a Minolta SPAD meter which analyzes the amount of light in a specific light spectrum passing through a leaf and converts that reading to a numerical value as an indicator of chlorophyll density in the leaf. Production was evaluated by sampling based on picking all fruit to be found on two plants and replicating this process eight times per treatment. All fruit was weighed, counted, and reported as grams total weight per two plants and grams total weight on average per fruit. All data rated as significant was done so utilizing the Least Significant Difference analysis at a 90% confidence level, such that values with a statistical significant identifier of the same letter are not significantly different. Results are shown in Tables 2-16 for the treatments designated with an S for soil application, along with accompanying statistical significance identifiers.

Example 2

An experiment was conducted to determine if a low concentration and low frequency application of mixotrophic *Chlorella* based composition to bell pepper plants (*Capsicum annuum*) by foliar application affected the yield of the plants. The foliar trial occurred in the same location, with the same treatments, and with the same design as the experiment of Example 1.

The mixotrophic *Chlorella* based composition was applied at a low concentration of 7 mL/gallon. The tested concentration of 7 mL/gallon diluted the composition which originally contained 10% solids by weight of mixotrophic *Chlorella* whole cells to the low percent solids content of only 0.018492%. The Acadian treatment was applied at a concentration of 18.9 mL/gallon. Five total treatments were applied at a low frequency (i.e., averaging about 21 days between applications), starting three weeks after plant establishment. The treatments occurred with 20 days between the first and second, 23 days between the second and third, 15 days between the third and fourth, and 27 days between the fourth and fifth. The low concentration and low frequency treatments were applied directly to the foliage at a rate of 25 gallons/acre with a backpack sprayer operating at 40 psi through a Hollow Co. nozzle size D-6.

All data rated as significant was done so utilizing the Least Significant Difference analysis at a 90% confidence level, such that values with a statistical significant identifier of the same letter are not significantly different. Results are shown in Tables 2-16 for the treatments designated with an F for foliar application, along with accompanying statistical significance identifiers. It was noted by the time the field was harvested many of the above mentioned unmarketable quality issues did occur and thus the ratio of unmarketable fruit was higher in this field than one might expect.

TABLE 2

Plant Sizing - Whole plant (grams) (A = early, B = later)

| | | Avg. A | | Increase over UTC | Avg. B | | Increase over UTC |
|---|---|---|---|---|---|---|---|
| 1 | UTC - untreated water check F | 4.3 | a | | 31.2 | a | |
| | UTC - untreated water check S | 4.4 | a | | 24.8 | | |
| 2 | Mixotrophic *Chlorella* sp. - Whole Cells F | 4.6 | a | 6% | 30.9 | a | −1% |
| | Mixotrophic *Chlorella* sp. - Whole Cells S | 4.4 | a | −1% | 26.7 | a | 8% |
| 3 | Grower Standard Product - Acadian Liquid Seaweed Concentrate F | 4.5 | a | 4% | 35.6 | a | 14% |
| | Grower Standard Product - Acadian Liquid Seaweed Concentrate S | 5.1 | a | 17% | 32.7 | a | 32% |

Table 2 shows that there was not statistical significance to the results of the mixotrophic *Chlorella* based composition treatments compared to the UTC regarding whole plant weight. The foliar application of mixotrophic *Chlorella* based composition performed better than the soil application at the first measurement and resulted in a 6% increase over the UTC but did not sustain the advantage at the second measurement. The soli application performed better at the second measurement than the foliar application and resulted in an 8% increase over the UTC.

TABLE 3

Plant Sizing - Root (grams) (A = earlier, B = later)

| | | Avg. A | | Increase over UTC | Avg. B | | Increase over UTC |
|---|---|---|---|---|---|---|---|
| 1 | UTC - untreated water check F | 0.6 | a | | 3.4 | a | |
| | UTC - untreated water check S | 0.6 | a | | 3.0 | | |
| 2 | Mixotrophic *Chlorella* sp. - Whole Cells F | 0.6 | a | 7% | 3.3 | a | −4% |
| | Mixotrophic *Chlorella* sp. - Whole Cells S | 0.7 | a | 8% | 3.3 | a | 9% |
| 3 | Grower Standard Product - Acadian Liquid Seaweed Concentrate F | 0.6 | a | 0% | 4.0 | a | 17% |
| | Grower Standard Product - Acadian Liquid Seaweed Concentrate S | 0.7 | a | 8% | 3.6 | a | 21% |

Table 3 shows that there was not statistical significance to the results of the mixotrophic *Chlorella* based composition treatments compared to the UTC regarding root weight. The foliar and soil applications of mixotrophic *Chlorella* based composition performed better than the UTC at the first measurement, with 7% and 8% increases over the UTC. The foliar application did not sustain this advantage at the second measurement, but the soil application maintained the advantage showing a 9% increase over the UTC.

TABLE 4

Plant Sizing - Shoot (grams) (A = earlier, B = later)

| | | Avg. A | | Increase over UTC | Avg. B | | Increase over UTC |
|---|---|---|---|---|---|---|---|
| 1 | UTC - untreated water check F | 3.8 | a | | 27.7 | a | |
| | UTC - untreated water check S | 3.7 | a | | 24.0 | | |
| 2 | Mixotrophic *Chlorella* sp. - Whole Cells F | 4.0 | a | 6% | 27.6 | a | 0% |
| | Mixotrophic *Chlorella* sp. - Whole Cells S | 3.7 | a | −2% | 23.5 | a | −2% |
| 3 | Grower Standard Product - Acadian Liquid Seaweed Concentrate F | 3.9 | a | 5% | 31.6 | a | 14% |
| | Grower Standard Product - Acadian Liquid Seaweed Concentrate S | 4.4 | a | 18% | 29.1 | a | 21% |

Table 4 shows that there was not statistical significance to the results of the mixotrophic *Chlorella* based composition treatments compared to the UTC regarding shoot weight. The foliar application of mixotrophic *Chlorella* based composition performed better than the UTC and soil application at the first measurement, with a 6% increases over the UTC. The foliar application did not sustain this advantage at the second measurement.

TABLE 5

Average Plant Chlorophyll Content (SPAD)

|   |   | A | B |   | Avg. | Increase over UTC |
|---|---|---|---|---|------|-------------------|
| 1 | UTC - untreated water check F | 64.7 | — 39.7 | a | 52.2 | |
|   | UTC - untreated water check S | | — 69.7 | ab | 69.7 | |
| 2 | Mixotrophic Chlorella sp. - Whole Cells F | 71.5 | — 36.4 | a | 54.0 | 3% |
|   | Mixotrophic Chlorella sp. - Whole Cells S | | — 70.2 | ab | 70.2 | 1% |
| 3 | Grower Standard Product - Acadian Liquid Seaweed Concentrate F | 70.6 | — 35.4 | a | 53.0 | 2% |
|   | Grower Standard Product - Acadian Liquid Seaweed Concentrate S | | — 64.5 | a | 64.5 | −7% |

Table 5 shows that there was not statistical significance to the results of the mixotrophic Chlorella based composition treatments compared to the UTC regarding chlorophyll content. The foliar and soil applications of mixotrophic Chlorella based composition performed within 3% of the UTC.

TABLE 6

Average Plant Vigor (Visual Scale 0-5)

|   |   | A |   | B |   | C |   | Avg. | Increase over UTC |
|---|---|---|---|---|---|---|---|------|-------------------|
| 1 | UTC - untreated water check F | 3.4 | a | 4.5 | a | 4.0 | a | 4.0 | |
|   | UTC - untreated water check S | 3.5 | a | 4.5 | a | | | 4.0 | |
| 2 | Mixotrophic Chlorella sp. - Whole Cells F | 3.2 | a | 4.1 | a | 4.0 | a | 3.8 | −5% |
|   | Mixotrophic Chlorella sp. - Whole Cells S | 4.0 | a | 4.0 | a | | | 4.0 | 0% |
| 3 | Grower Standard Product - Acadian Liquid Seaweed Concentrate F | 3.2 | a | 4.3 | a | 4.0 | a | 3.8 | −3% |
|   | Grower Standard Product - Acadian Liquid Seaweed Concentrate S | 3.5 | a | 4.0 | a | | | 3.8 | −6% |

Table 6 shows that there was not statistical significance to the results of the mixotrophic Chlorella based composition treatments compared to the UTC regarding plant vigor, nor was there a numerical advantage.

TABLE 7

Total Unmarketable Plant Weight per Plot (grams)

|   |   | Avg. | | Increase over UTC |
|---|---|------|---|-------------------|
| 1 | UTC - untreated water check F | 1895.0 | a | |
|   | UTC - untreated water check S | 963.8 | a | |
| 2 | Mixotrophic Chlorella sp. - Whole Cells F | 1803.1 | a | −5% |
|   | Mixotrophic Chlorella sp. - Whole Cells S | 179.4 | b | −81% |
| 3 | Grower Standard Product - Acadian Liquid Seaweed Concentrate F | 1580.6 | a | −17% |
|   | Grower Standard Product - Acadian Liquid Seaweed Concentrate S | 66.9 | b | −93% |

Table 7 shows that the soil application of the mixotrophic Chlorella based composition had a statistically significant decrease in unmarketable plant weight compared to the UTC, and the foliar application results were not statistically significant compared to the UTC.

TABLE 8

Total Unmarketable Plant Yield per Plot (number)

|   |   | Avg. | | Increase over UTC |
|---|---|------|---|-------------------|
| 1 | UTC - untreated water check F | 10.8 | a | |
|   | UTC - untreated water check S | 6.0 | a | |
| 2 | Mixotrophic Chlorella sp. - Whole Cells F | 9.8 | a | −9% |
|   | Mixotrophic Chlorella sp. - Whole Cells S | 1.9 | b | −69% |
| 3 | Grower Standard Product - Acadian Liquid Seaweed Concentrate F | 9.1 | a | −15% |
|   | Grower Standard Product - Acadian Liquid Seaweed Concentrate S | 1.1 | b | −81% |

Table 8 shows that the soil application of the mixotrophic Chlorella based composition had a statistically significant decrease in unmarketable plant yield compared to the UTC, and the foliar application results were not statistically significant compared to the UTC.

TABLE 9

Total Unmarketable Fruit Weight per Plot (grams)

|   |   | Avg. | | Increase over UTC |
|---|---|------|---|-------------------|
| 1 | UTC - untreated water check F | 178.5 | a | |
|   | UTC - untreated water check S | 56.2 | a | |
| 2 | Mixotrophic Chlorella sp. - Whole Cells F | 182.8 | a | 2% |
|   | Mixotrophic Chlorella sp. - Whole Cells S | 57.6 | a | 2% |
| 3 | Grower Standard Product - Acadian Liquid Seaweed Concentrate F | 173.2 | a | −3% |
|   | Grower Standard Product - Acadian Liquid Seaweed Concentrate S | 35.3 | a | −37% |

Table 9 shows that the soil and foliar applications of the mixotrophic Chlorella based composition were not statistically significant compared to the UTC for unmarketable fruit weight, but both showed a numerical increase of 2% over the UTC. The soil application of mixotrophic Chlorella based composition also outperformed the Acadian product, which showed a 37% decrease compared to the UTC.

TABLE 10

Total Marketable Plant Weight per Plot (grams)

|   |   | Avg. | | Increase over UTC |
|---|---|---|---|---|
| 1 | UTC - untreated water check F | 120.6 | a | |
|   | UTC - untreated water check S | 317.5 | c | |
| 2 | Mixotrophic *Chlorella* sp. - Whole Cells F | 386.3 | a | 220% |
|   | Mixotrophic *Chlorella* sp. - Whole Cells S | 1224.4 | a | 286% |
| 3 | Grower Standard Product - Acadian Liquid Seaweed Concentrate F | 502.5 | a | 317% |
|   | Grower Standard Product - Acadian Liquid Seaweed Concentrate S | 1233.1 | a | 288% |

Table 10 shows that the results of the soil application of the mixotrophic *Chlorella* based composition were statistically significant compared to the UTC for marketable plant weight, and both soil and foliar applications showed large numerical increases of 286% and 220% over the UTC, which was comparable with the commercially successful Acadian product. These results show the small amounts of the mixotrophic *Chlorella* based composition at a low concentration and low frequency application are effective for not only improving plant weight, put improving plant weight in the higher quality plants (i.e., marketable) when applied to the soil or foliage.

TABLE 11

Total Marketable Plant Yield per Plot (number)

|   |   | Avg. | | Increase over UTC |
|---|---|---|---|---|
| 1 | UTC - untreated water check F | 0.6 | a | |
|   | UTC - untreated water check S | 2.3 | a | |
| 2 | Mixotrophic *Chlorella* sp. - Whole Cells F | 2.0 | a | 220% |
|   | Mixotrophic *Chlorella* sp. - Whole Cells S | 6.8 | a | 200% |
| 3 | Grower Standard Product - Acadian Liquid Seaweed Concentrate F | 2.8 | a | 340% |
|   | Grower Standard Product - Acadian Liquid Seaweed Concentrate S | 7.1 | a | 217% |

Table 11 shows that the results of the soil and foliar applications of the mixotrophic *Chlorella* based composition showed large numerical increases of 200% and 220% over the UTC, which was comparable with the commercially successful Acadian product. These results show the small amounts of the mixotrophic *Chlorella* based composition at a low concentration and low frequency application are effective for not only improving plant yield, put improving plant yield in the higher quality plants (i.e., marketable) when applied to the soil or foliage.

TABLE 12

Total Marketable Fruit Weight per Plot (grams)

|   |   | Avg. | | Increase over UTC |
|---|---|---|---|---|
| 1 | UTC - untreated water check F | 73.1 | a | |
|   | UTC - untreated water check S | 123.7 | b | |
| 2 | Mixotrophic *Chlorella* sp. - Whole Cells F | 43.8 | a | −40% |
|   | Mixotrophic *Chlorella* sp. - Whole Cells S | 182.9 | a | 48% |
| 3 | Grower Standard Product - Acadian Liquid Seaweed Concentrate F | 115.8 | a | 58% |
|   | Grower Standard Product - Acadian Liquid Seaweed Concentrate S | 66.9 | a | −46% |

Table 12 shows that the results of the soil application of the mixotrophic *Chlorella* based composition were statistically significant compared to the UTC for marketable fruit weight. The soil application of mixotrophic *Chlorella* based composition also showed a numerical increase of 48% over the UTC. The soil application of *Chlorella* based composition also outperformed the Acadian product, which showed a 46% decrease compared to the UTC. These results show the small amounts of the mixotrophic *Chlorella* based composition at a low concentration and low frequency application are effective for not only improving fruit weight, put improving fruit weight in the higher quality plants (i.e., marketable) when applied to the soil.

TABLE 13

Total Production Plant Weight per Plot (grams)

|   |   | Avg. | | Increase over UTC |
|---|---|---|---|---|
| 1 | UTC - untreated water check F | 2015.6 | a | |
|   | UTC - untreated water check S | 656.3 | c | |
| 2 | Mixotrophic *Chlorella* sp. - Whole Cells F | 2189.4 | a | 9% |
|   | Mixotrophic *Chlorella* sp. - Whole Cells S | 1403.8 | a | 114% |
| 3 | Grower Standard Product - Acadian Liquid Seaweed Concentrate F | 2083.1 | a | 3% |
|   | Grower Standard Product - Acadian Liquid Seaweed Concentrate S | 1300.0 | a | 98% |

Table 13 shows that the results of the soil application of the mixotrophic *Chlorella* based composition were statistically significant compared to the UTC for production plant weight. The soil application of mixotrophic *Chlorella* based composition also showed a numerical increase of 114% over the UTC, with the foliar application showing a 9% increase over the UTC, which were both comparable to the Acadian product. These results show the small amounts of the mixotrophic *Chlorella* based composition at a low concentration and low frequency application are effective for not only total production plant weight when applied to the soil.

TABLE 14

Total Production Plant Yield per Plot (number)

|   |   | Avg. | | Increase over UTC |
|---|---|---|---|---|
| 1 | UTC - untreated water check F | 11.4 | a | |
|   | UTC - untreated water check S | 8.3 | a | |
| 2 | Mixotrophic *Chlorella* sp. - Whole Cells F | 11.8 | a | 3% |

TABLE 14-continued

Total Production Plant Yield per Plot (number)

| | | Avg. | | Increase over UTC |
|---|---|---|---|---|
| | Mixotrophic *Chlorella* sp. - Whole Cells S | 8.6 | a | 5% |
| 3 | Grower Standard Product - Acadian Liquid Seaweed Concentrate F | 11.9 | a | 4% |
| | Grower Standard Product - Acadian Liquid Seaweed Concentrate S | 8.3 | a | 0% |

Table 14 shows that the results of the soil and foliar applications of the mixotrophic *Chlorella* based composition were not statistically significant compared to the UTC for production plant yield, but did show numerical increases of 5% and 3% over the UTC.

TABLE 15

Average Production Fruit Weight per Plot (grams)

| | | Avg. | | Increase over UTC |
|---|---|---|---|---|
| 1 | UTC - untreated water check F | 179.0 | a | |
| | UTC - untreated water check S | 80.5 | b | |
| 2 | Mixotrophic *Chlorella* sp. - Whole Cells F | 189.6 | a | 6% |
| | Mixotrophic *Chlorella* sp. - Whole Cells S | 167.0 | a | 107% |
| 3 | Grower Standard Product - Acadian Liquid Seaweed Concentrate F | 174.1 | a | −3% |
| | Grower Standard Product - Acadian Liquid Seaweed Concentrate S | 159.8 | a | 98% |

Table 15 shows that the results of the soil application of the mixotrophic *Chlorella* based composition were statistically significant compared to the UTC for production fruit weight. The soil application of mixotrophic *Chlorella* based composition also showed a numerical increase of 117% over the UTC, with the foliar application showing a 6% increase over the UTC, both of which were comparable to the Acadian product. These results show the small amounts of the mixotrophic *Chlorella* based composition at a low concentration and low frequency application are effective for not only total production fruit weight when applied to the soil or foliage.

TABLE 16

Utilization (%, ratio of marketable fruit to total fruit produced by weight)

| | | Avg. | | Increase over UTC |
|---|---|---|---|---|
| 1 | UTC - untreated water check F | 6.5 | a | |
| | UTC - untreated water check S | 45.0 | b | |
| 2 | Mixotrophic *Chlorella* sp. - Whole Cells F | 11.8 | a | 81% |
| | Mixotrophic *Chlorella* sp. - Whole Cells S | 88.3 | a | 96% |
| 3 | Grower Standard Product - Acadian Liquid Seaweed Concentrate F | 18.3 | a | 181% |
| | Grower Standard Product - Acadian Liquid Seaweed Concentrate S | 94.6 | a | 110% |

Table 16 shows that the results of the soil application of the mixotrophic *Chlorella* based composition were statistically significant compared to the UTC for utilization percentage (ratio of marketable fruit to total fruit produced by weight). The soil application of mixotrophic *Chlorella* based composition also showed a numerical increase of 96% over the UTC, with the foliar application showing an 81% increase over the UTC. These results show the small amounts of the mixotrophic *Chlorella* based composition at a low concentration and low frequency application are effective for improving the total quality of the field when applied to the soil or foliage.

Example 3

An experiment was conducted to determine if a low concentration and low frequency application of a mixotrophic *Chlorella* based composition to gavilon tomato plants (*Solanum lycopersicum*) by soil application affected the yield of the plants. Tomatoes are also members of the Solanaceae plant family. The soil application trial occurred in the same location, with the same treatments, and with the same design as the experiment of Example 1. The tomato plants were grown as a bush on the ground for this experiment.

The mixotrophic *Chlorella* based composition was applied at a low concentration of 37.85 mL/gallon. The tested concentration of 37.85 mL/gallon diluted the composition which originally contained 10% solids by weight of mixotrophic *Chlorella* whole cells to the low percent solids content of only 0.099989%. The Acadian treatment was applied at a concentration of 18.9 mL/gallon. Five total treatments were applied at a low frequency (i.e., averaging about 23 days between applications), starting three weeks after plant establishment. The treatments occurred with 19 days between the first and second, 29 days between the second and third, 23 days between the third and fourth, and 21 days between the fourth and fifth. The low concentration and low frequency treatments were applied by injection into a low volume irrigation drip system at a rate of 100 gallons/acre using a Hypro pump operating at 25 psi.

All data rated as significant was done so utilizing the Least Significant Difference analysis at a 90% confidence level, such that values with a statistical significant identifier of the same letter are not significantly different. Results are shown in tables 17-28 for the treatments designated with an S for soil application, along with accompanying statistical significance identifiers.

Example 4

An experiment was conducted to determine if a low concentration and low frequency application of mixotrophic *Chlorella* based composition to gavilon tomato plants (*Solanum lycopersicum*) by foliar application affected the yield of the plants. The foliar trial occurred in the same location, with the same treatments, and with the same design as the experiment of Example 2. The tomato plants were grown on stakes for this experiment.

The mixotrophic *Chlorella* based composition was applied at a low concentration of 7 mL/gallon. The tested concentration of 7 mL/gallon diluted the composition which originally contained 10% solids by weight of mixotrophic *Chlorella* whole cells to the low percent solids content of only 0.018492%. The Acadian treatment was applied at a concentration of 18.9 mL/gallon. Five total treatments were applied at a low frequency (i.e., averaging about 21 days between applications), starting three weeks after plant establishment. The treatments occurred with 19 days between the first and second, 21 days between the second and third, 23 days between the third and fourth, and 21 days between the fourth and fifth. The low concentration and low frequency treatments were applied directly to the foliage at a rate of 25 gallons/acre with a backpack sprayer operating at 40 psi through a Hollow Co. nozzle size D-6.

All data rated as significant was done so utilizing the Least Significant Difference analysis at a 90% confidence level, such that values with a statistical significant identifier of the same letter are not significantly different. Results are shown in tables 17-28 for the treatments designated with an F for foliar application, along with accompanying statistical significance identifiers.

TABLE 17

Average Plant Chlorophyll Content (SPAD)

| | | A | | B | | Avg. | Increase over UTC |
|---|---|---|---|---|---|---|---|
| 1 | UTC - untreated water check F | 52.7 | a | 48.0 | a | 50.4 | |
| | UTC - untreated water check S | 44.6 | a | | | 44.6 | |
| 2 | Mixotrophic Chlorella sp. - Whole Cells F | 54.6 | a | 45.4 | a | 50.0 | −1% |
| | Mixotrophic Chlorella sp. - Whole Cells S | 44.5 | a | | | 44.5 | 0% |
| 3 | Grower Standard Product - Acadian Liquid Seaweed Concentrate F | 53.9 | a | 46.2 | a | 50.1 | −1% |
| | Grower Standard Product - Acadian Liquid Seaweed Concentrate S | 41.8 | a | | | 41.8 | −6% |

Table 17 shows that there was not statistical significance to the results of the mixotrophic Chlorella based composition treatments compared to the UTC regarding chlorophyll content, nor a numerical increase.

TABLE 18

Average Plant Vigor (Visual Scale 0-5)

| | | A | | B | | Avg. | Increase over UTC |
|---|---|---|---|---|---|---|---|
| 1 | UTC - untreated water check F | 4.9 | a | 3.9 | a | 4.4 | |
| | UTC - untreated water check S | 4.2 | a | | | 4.2 | |
| 2 | Mixotrophic Chlorella sp. - Whole Cells F | 5.0 | a | 3.6 | a | 4.3 | −2% |
| | Mixotrophic Chlorella sp. - Whole Cells S | 4.5 | a | | | 4.5 | 7% |
| 3 | Grower Standard Product - Acadian Liquid Seaweed Concentrate F | 4.9 | a | 4.1 | a | 4.5 | 2% |
| | Grower Standard Product - Acadian Liquid Seaweed Concentrate S | 4.1 | a | | | 4.1 | −2% |

Table 18 shows that there was not statistical significance to the results of the mixotrophic Chlorella based composition treatments compared to the UTC regarding plant vigor, however the soil application showed a 7% increase over the UTC.

TABLE 19

Total Unmarketable Plant Weight per Plot (grams)

| | | Avg. | | Increase over UTC |
|---|---|---|---|---|
| 1 | UTC - untreated water check F | 205.8 | a | |
| | UTC - untreated water check S | 2156.0 | a | |
| 2 | Mixotrophic Chlorella sp. - Whole Cells F | 139.2 | a | −32% |
| | Mixotrophic Chlorella sp. - Whole Cells S | 2279.2 | a | 6% |
| 3 | Grower Standard Product - Acadian Liquid Seaweed Concentrate F | 162.5 | a | −21% |
| | Grower Standard Product - Acadian Liquid Seaweed Concentrate S | 997.5 | b | −54% |

Table 19 shows that the application of the mixotrophic Chlorella based composition did not have a statistically significant decrease in unmarketable plant weight compared to the UTC, however the foliar application showed a 32% decrease over the UTC. The soil application of mixotrophic Chlorella based composition showed a 6% increase over the UTC, while the commercially successful Acadian product soil application showed a 54% decrease.

TABLE 20

Total Unmarketable Plant Yield per Plot (number)

| | | Avg. | | Increase over UTC |
|---|---|---|---|---|
| 1 | UTC - untreated water check F | 5.8 | a | |
| | UTC - untreated water check S | 49.3 | a | |
| 2 | Mixotrophic Chlorella sp. - Whole Cells F | 3.0 | a | −49% |
| | Mixotrophic Chlorella sp. - Whole Cells S | 47.7 | a | −3% |
| 3 | Grower Standard Product - Acadian Liquid Seaweed Concentrate F | 3.0 | a | −49% |
| | Grower Standard Product - Acadian Liquid Seaweed Concentrate S | 28.5 | bc | −42% |

Table 20 shows that the application of the mixotrophic Chlorella based composition did not have a statistically significant decrease in unmarketable plant yield compared to the UTC, however the foliar application showed a 49% decrease and the soil application showed a 3% decrease with respect to the UTC, which was smaller than the 42% decrease of the Acadian product soil application.

TABLE 21

Total Unmarketable Fruit Weight per Plot (grams)

| | | Avg. | | Increase over UTC |
|---|---|---|---|---|
| 1 | UTC - untreated water check F | 29.6 | a | |
| | UTC - untreated water check S | 45.8 | a | |
| 2 | Mixotrophic Chlorella sp. - Whole Cells F | 27.5 | a | −7% |
| | Mixotrophic Chlorella sp. - Whole Cells S | 47.4 | a | 3% |

TABLE 21-continued

Total Unmarketable Fruit Weight per Plot (grams)

| | | Avg. | | Increase over UTC |
|---|---|---|---|---|
| 3 | Grower Standard Product - Acadian Liquid Seaweed Concentrate F | 35.5 | a | 20% |
| | Grower Standard Product - Acadian Liquid Seaweed Concentrate S | 34.8 | a | −24% |

Table 21 shows that the soil and foliar applications of the mixotrophic *Chlorella* based composition were not statistically significant compared to the UTC for unmarketable fruit weight, but the soil application showed a 3% increase, while the Acadian product showed a 24% decrease, and the foliar application showed a 7% decrease with respect to the UTC.

TABLE 22

Total Marketable Plant Weight per Plot (grams)

| | | Avg. | | Increase over UTC |
|---|---|---|---|---|
| 1 | UTC - untreated water check F | 8702.5 | a | |
| | UTC - untreated water check S | 7616.7 | a | |
| 2 | Mixotrophic *Chlorella* sp. - Whole Cells F | 8317.5 | a | −4% |
| | Mixotrophic *Chlorella* sp. - Whole Cells S | 8160.8 | a | 7% |
| 3 | Grower Standard Product - Acadian Liquid Seaweed Concentrate F | 7731.7 | a | −11% |
| | Grower Standard Product - Acadian Liquid Seaweed Concentrate S | 7828.3 | a | 3% |

Table 22 shows that the results of the application of the mixotrophic *Chlorella* based composition were not statistically significant compared to the UTC for marketable plant weight, however the soil application showed a 7% increase over the UTC.

TABLE 23

Total Marketable Plant Yield per Plot (number)

| | | Avg. | | Increase over UTC |
|---|---|---|---|---|
| 1 | UTC - untreated water check F | 120.8 | a | |
| | UTC - untreated water check S | 103.5 | a | |
| 2 | Mixotrophic *Chlorella* sp. - Whole Cells F | 103.0 | a | −15% |
| | Mixotrophic *Chlorella* sp. - Whole Cells S | 115.3 | a | 11% |
| 3 | Grower Standard Product - Acadian Liquid Seaweed Concentrate F | 107.7 | a | −11% |
| | Grower Standard Product - Acadian Liquid Seaweed Concentrate S | 118.0 | a | 14% |

Table 23 shows that the results of the soil and foliar applications of the mixotrophic *Chlorella* based composition were not statistically significant compared to the UTC for marketable plant yield, however the soil application showed an 11% increase over the UTC.

TABLE 24

Total Marketable Fruit Weight per Plot (grams)

| | | Avg. | | Increase over UTC |
|---|---|---|---|---|
| 1 | UTC - untreated water check F | 72.2 | b | |
| | UTC - untreated water check S | 74.5 | a | |
| 2 | Mixotrophic *Chlorella* sp. - Whole Cells F | 80.5 | a | 11% |
| | Mixotrophic *Chlorella* sp. - Whole Cells S | 70.1 | a | −6% |
| 3 | Grower Standard Product - Acadian Liquid Seaweed Concentrate F | 72.0 | b | 0% |
| | Grower Standard Product - Acadian Liquid Seaweed Concentrate S | 65.7 | a | −12% |

Table 24 shows that the results of the foliar application of the mixotrophic *Chlorella* based composition were statistically significant compared to the UTC and Acadian product for marketable fruit weight, and resulted in an 11% increase over the UTC. These results show the small amounts of the mixotrophic *Chlorella* based composition at a low concentration and low frequency application are effective for not only improving fruit weight, put improving fruit weight in the higher quality plants (i.e., marketable) when applied to the foliage.

TABLE 25

Total Production Plant Weight per Plot (grams)

| | | Avg. | | Increase over UTC |
|---|---|---|---|---|
| 1 | UTC - untreated water check F | 8908.3 | a | |
| | UTC - untreated water check S | 9272.7 | a | |
| 2 | Mixotrophic *Chlorella* sp. - Whole Cells F | 8456.7 | a | −5% |
| | Mixotrophic *Chlorella* sp. - Whole Cells S | 10440.0 | a | 13% |
| 3 | Grower Standard Product - Acadian Liquid Seaweed Concentrate F | 7894.2 | a | −11% |
| | Grower Standard Product - Acadian Liquid Seaweed Concentrate S | 8825.8 | a | −5% |

Table 25 shows that the results of the soil application of the mixotrophic *Chlorella* based composition were not statistically significant compared to the UTC for production plant weight, however the soil application resulted in a numerical increase of 13% over the UTC while the Acadian product showed a 5% decrease.

TABLE 26

Total Production Plant Yield per Plot (number)

| | | Avg. | | Increase over UTC |
|---|---|---|---|---|
| 1 | UTC - untreated water check F | 126.7 | a | |
| | UTC - untreated water check S | 152.8 | ab | |
| 2 | Mixotrophic *Chlorella* sp. - Whole Cells F | 110.2 | a | −13% |
| | Mixotrophic *Chlorella* sp. - Whole Cells S | 163.0 | a | 7% |

TABLE 26-continued

Total Production Plant Yield per Plot (number)

| | | Avg. | | Increase over UTC |
|---|---|---|---|---|
| 3 | Grower Standard Product - Acadian Liquid Seaweed Concentrate F | 110.7 | a | −13% |
| | Grower Standard Product - Acadian Liquid Seaweed Concentrate S | 146.5 | abc | −4% |

Table 26 shows that the results of the soil and foliar applications of the mixotrophic *Chlorella* based composition were not statistically significant compared to the UTC for production plant yield, but the soil application showed an increase of 7% over the UTC, with the Acadian product showing a 4% decrease.

TABLE 27

Average Production Fruit Weight per Plot (grams)

| | | Avg. | | Increase over UTC |
|---|---|---|---|---|
| 1 | UTC - untreated water check F | 70.7 | a | |
| | UTC - untreated water check S | 64.8 | a | |
| 2 | Mixotrophic *Chlorella* sp. - Whole Cells F | 76.7 | a | 9% |
| | Mixotrophic *Chlorella* sp. - Whole Cells S | 63.1 | a | −3% |
| 3 | Grower Standard Product - Acadian Liquid Seaweed Concentrate F | 71.6 | a | 1% |
| | Grower Standard Product - Acadian Liquid Seaweed Concentrate S | 59.4 | a | −8% |

Table 27 shows that the results of the foliar application of the mixotrophic *Chlorella* based composition were not statistically significant compared to the UTC for production fruit weight, however the foliar application showed a numerical increase of 9% over the UTC.

TABLE 28

Utilization (%, the ratio of marketable fruit to total fruit produced by weight)

| | | Avg. | | Increase over UTC |
|---|---|---|---|---|
| 1 | UTC - untreated water check F | 97.5 | a | |
| | UTC - untreated water check S | 76.8 | c | |
| 2 | Mixotrophic *Chlorella* sp. - Whole Cells F | 98.3 | a | 1% |
| | Mixotrophic *Chlorella* sp. - Whole Cells S | 77.2 | c | 0% |
| 3 | Grower Standard Product - Acadian Liquid Seaweed Concentrate F | 98.0 | a | 1% |
| | Grower Standard Product - Acadian Liquid Seaweed Concentrate S | 88.7 | a | 15% |

Table 28 shows that the results of the application of the mixotrophic *Chlorella* based composition were not statistically significant compared to the UTC for utilization percentage (ratio of marketable fruit to total fruit produced by weight).

Example 5

An experiment was conducted to determine if a low concentration and low frequency application of mixotrophic *Chlorella* based composition to heirloom tomato (cv German striped) plants by foliar application affected the initial growth and sizing of the plants. Tomato seeds (*Solanum lycopersicum*) were planted in trays with standard soilless plant potting soil mix and grown in a nursery greenhouse. Treatments of a mixotrophic *Chlorella* based composition and a commercially available reference product were compared to an untreated control (UTC) and are listed in Table 28, with duplicate treatments of the mixotrophic *Chlorella* based composition being tested. A commercially available macroalgae extract based product was obtained from Acadian Seaplants Limited (30 Brown Avenue, Dartmouth, Nova Scotia, Canada, B3B 1X8) for comparison.

TABLE 29

| Treatment No. | Treatment Description |
|---|---|
| 1 | UTC - untreated water check |
| 2 | Mixotrophic *Chlorella* sp. - Whole Cells |
| 3 | Mixotrophic *Chlorella* sp. - Whole Cells |
| 4 | Grower Standard Product - Acadian Liquid Seaweed Concentrate |

The mixotrophic *Chlorella* based composition was pasteurized, normalized to 10% solids, and stabilized with phosphoric acid ($H_3PO_4$) and potassium sorbate ($C_6H_7KO_2$), with remaining balance consisting of water. The mixotrophic *Chlorella* whole cells were not previously subjected to a purification process to isolate the cells from the microalgae culturing medium, nor were the cells previously subjected to a drying, extraction, or other process that may lyse or disrupt the cell walls. The composition comprising mixotrophic *Chlorella* used in the treatments of this experiment were not analyzed to quantify bacteria in the compositions, however aerobic plate counts for previous compositions prepared with the same components in the same manner contained 40,000-400,000 CFU/mL. The mixotrophic *Chlorella* composition was previously frozen and thawed, and was incorporated into the liquid composition for treatments used in this experiment after cold storage following being harvested from the microalgae culturing system.

The mixotrophic *Chlorella* based composition treatments were applied to the plants at a low concentration of 4 mL/gallon. The tested concentration of 4 mL/gallon diluted the composition which originally contained 10% solids by weight of mixotrophic *Chlorella* whole cells to the low percent solids content of only 0.010567%. The Acadian treatment was applied to plants at a concentration of 9.46 mL/gallon. The low concentration and low frequency treatment method consisted of directly spraying the foliage of the plants a rate of 25 gallons/acre using a spray bottle. A total of three treatments were applied with the first application occurring three weeks after planting (7-10 days after emergence). The second treatment was applied five days after the first, and the third treatment was applied six days after the second.

Each treatment was applied to a 14 inch by 14 inch planting flats containing plants resulting from 25-30 seeds. There were eight replicates of each treatment. All seeds were planted in a standard soilless potting plant mix. Each plant analyzed was counted as a replicate with eight replicates considered for teach treatment evaluation. Analysis occurred after the second treatment and after the third treatment. The chlorophyll content was estimated by SPAD (Soil-Plant Analysis Development) value, a numeric value provided by a Minolta SPAD meter which analyzes the amount of light in a specific light spectrum passing through a leaf and converts that reading to a numerical value as an indicator of chlorophyll density in the leaf. The experiment was conducted inside a greenhouse with all seeds and treatments subjected to the same controlled conditions including temperature and light. All trays were treated with the same amount of water throughout the experiment. No additional nutrients were provided to the plants during the experiment. All data rated as significant was done so utilizing the New Duncan's Multiple Test Range at a 90% confidence level, such that values with a statistical significant identifier of the same letter are not significantly different. Results are shown in Tables 30-35 designated with an F for foliar application, with accompanying statistical significance grouping identifiers.

Example 6

An experiment was conducted to determine if a low concentration and low frequency application of mixotrophic *Chlorella* based composition to heirloom tomato (cv German striped) plants (*Solanum lycopersicum*) by soil application affected the initial growth and sizing of the plants. The soil application trial occurred in the same location, with the same treatments, and with the same design as the experiment in Example 5.

The mixotrophic *Chlorella* based composition treatments were applied to the plants at a low concentration of 4.73 mL/gallon. The tested concentration of 4.73 mL/gallon diluted the composition which originally contained 10% solids by weight of mixotrophic *Chlorella* whole cells to the low percent solids content of only 0.012495%. The Acadian treatment was applied to plants at a concentration of 9.46 mL/gallon. The low concentration and low frequency treatment method consisted of drenching the soil at a rate of 100 gallons/acre. A total of three treatments were applied with the first application occurring two weeks after planting (7-10 days after emergence). The second treatment was applied nine days after the first, and the third treatment was applied five days after the second. All data rated as significant was done so utilizing the New Duncan's Multiple Test Range at a 90% confidence level, such that values with a statistical significant identifier of the same letter are not significantly different. Results are shown in Tables 30-35 designated with an S for soil application, with accompanying statistical significance grouping identifiers.

TABLE 30

Nursery Tomato Plant Sizing - Plant Height (inches)

| | | Avg. | | Increase over UTC |
|---|---|---|---|---|
| 1 | UTC - untreated water check F | 6.00 | cde | |
| | UTC - untreated water check S | 5.85 | ab | |
| 2 | Mixotrophic *Chlorella* sp. - Whole Cells F | 5.27 | fg | −12% |
| | Mixotrophic *Chlorella* sp. - Whole Cells S | 5.20 | def | −11% |
| 3 | Mixotrophic *Chlorella* sp. - Whole Cells F | 6.13 | abcd | 2% |
| | Mixotrophic *Chlorella* sp. - Whole Cells S | 5.52 | bcd | −6% |

TABLE 30-continued

Nursery Tomato Plant Sizing - Plant Height (inches)

| | | Avg. | | Increase over UTC |
|---|---|---|---|---|
| 4 | Grower Standard Product - Acadian Liquid Seaweed Concentrate F | 5.94 | de | −1% |
| | Grower Standard Product - Acadian Liquid Seaweed Concentrate S | 5.67 | abc | −3% |

As shown in Table 30, the applications of mixotrophic *Chlorella* based composition did not result in significant difference from the UTC regarding plant height.

TABLE 31

Nursery Tomato Plant Sizing - Leaf Number

| | | Avg. | | Increase over UTC |
|---|---|---|---|---|
| 1 | UTC - untreated water check F | 5.1 | a | |
| | UTC - untreated water check S | 4.5 | a | |
| 2 | Mixotrophic *Chlorella* sp. - Whole Cells F | 4.9 | a | −2% |
| | Mixotrophic *Chlorella* sp. - Whole Cells S | 4.5 | a | 0% |
| 3 | Mixotrophic *Chlorella* sp. - Whole Cells F | 5.3 | a | 4% |
| | Mixotrophic *Chlorella* sp. - Whole Cells S | 4.4 | a | −3% |
| 4 | Grower Standard Product - Acadian Liquid Seaweed Concentrate F | 4.9 | a | −2% |
| | Grower Standard Product - Acadian Liquid Seaweed Concentrate S | 4.6 | a | 1% |

As shown in Table 31, the applications of mixotrophic *Chlorella* based composition did not result in significant difference from the UTC regarding leaf number, however the foliar application of treatment 3 resulted in a 4% increase over the UTC.

TABLE 32

Nursery Tomato Chlorophyll Content (SPAD)

| | | Avg. | | Increase over UTC |
|---|---|---|---|---|
| 1 | UTC - untreated water check F | 25.9 | f | |
| | UTC - untreated water check S | 30.4 | a | |
| 2 | Mixotrophic *Chlorella* sp. - Whole Cells F | 32.1 | bcd | 24% |
| | Mixotrophic *Chlorella* sp. - Whole Cells S | 30.7 | a | 1% |
| 3 | Mixotrophic *Chlorella* sp. - Whole Cells F | 34.0 | ab | 31% |
| | Mixotrophic *Chlorella* sp. - Whole Cells S | 32.7 | a | 8% |
| 4 | Grower Standard Product - Acadian Liquid Seaweed Concentrate F | 34.5 | ab | 33% |
| | Grower Standard Product - Acadian Liquid Seaweed Concentrate S | 30.6 | a | 1% |

As shown in Table 32, the foliar application of mixotrophic *Chlorella* based composition resulted in a significant difference from the UTC regarding chlorophyll content, showing an increase of 24% and 31% over the UTC. The soil application also showed increases of 1% and 8% over the UTC.

These results show the small amounts of the mixotrophic *Chlorella* based composition at a low concentration and low frequency application are effective at improving chlorophyll content in plants when applied to the foliage.

TABLE 33

Nursery Tomato Plant Sizing - Whole Plant Weight (grams)

| | | Avg. | | Increase over UTC |
|---|---|---|---|---|
| 1 | UTC - untreated water check F | 6.8 | d | |
| | UTC - untreated water check S | 7.1 | a | |
| 2 | Mixotrophic *Chlorella* sp. - Whole Cells F | 6.2 | d | −8% |
| | Mixotrophic *Chlorella* sp. - Whole Cells S | 5.3 | cdefg | −26% |
| 3 | Mixotrophic *Chlorella* sp. - Whole Cells F | 10.6 | ab | 56% |
| | Mixotrophic *Chlorella* sp. - Whole Cells S | 6.5 | ab | −8% |
| 4 | Grower Standard Product - Acadian Liquid Seaweed Concentrate F | 8.9 | abc | 31% |
| | Grower Standard Product - Acadian Liquid Seaweed Concentrate S | 4.6 | efgh | −35% |

As shown in Table 33, the foliar application of mixotrophic *Chlorella* based composition in treatment 3 resulted in a significant difference from the UTC regarding whole plant weight, showing an increase of 56% over the UTC. The foliar application of the Acadian product performed lower, showing only a 31% increase over the UTC. These results show the small amounts of the mixotrophic *Chlorella* based composition at a low concentration and low frequency application are effective at improving whole plant weight when applied to the foliage.

TABLE 34

Nursery Tomato Plant Sizing - Root Weight (grams)

| | | Avg. | | Increase over UTC |
|---|---|---|---|---|
| 1 | UTC - untreated water check F | 2.2 | bc | |
| | UTC - untreated water check S | 2.8 | a | |
| 2 | Mixotrophic *Chlorella* sp. - Whole Cells F | 1.9 | c | −12% |
| | Mixotrophic *Chlorella* sp. - Whole Cells S | 2.1 | bc | −24% |
| 3 | Mixotrophic *Chlorella* sp. - Whole Cells F | 3.3 | a | 51% |
| | Mixotrophic *Chlorella* sp. - Whole Cells S | 1.9 | cd | −30% |
| 4 | Grower Standard Product - Acadian Liquid Seaweed Concentrate F | 2.8 | ab | 28% |
| | Grower Standard Product - Acadian Liquid Seaweed Concentrate S | 1.5 | ef | −47% |

As shown in Tables 34, the foliar application of mixotrophic *Chlorella* based composition in treatment 3 resulted in a significant difference from the UTC regarding root weight, showing an increase of 51% over the UTC in treatment 3. The foliar application of the Acadian product performed lower, showing only a 28% increase over the UTC. These results show the small amounts of the mixotrophic *Chlorella* based composition at a low concentration and low frequency application are effective at improving root weight in plants when applied to the foliage.

TABLE 35

Nursery Tomato Plant Sizing - Shoot Weight (grams)

| | | Avg. | | Increase over UTC |
|---|---|---|---|---|
| 1 | UTC - untreated water check F | 4.6 | cde | |
| | UTC - untreated water check S | 4.3 | a | |
| 2 | Mixotrophic *Chlorella* sp. - Whole Cells F | 4.3 | e | −6% |
| | Mixotrophic *Chlorella* sp. - Whole Cells S | 3.2 | cde | −27% |
| 3 | Mixotrophic *Chlorella* sp. - Whole Cells F | 7.3 | a | 60% |
| | Mixotrophic *Chlorella* sp. - Whole Cells S | 4.6 | a | 6% |
| 4 | Grower Standard Product - Acadian Liquid Seaweed Concentrate F | 6.1 | ab | 33% |
| | Grower Standard Product - Acadian Liquid Seaweed Concentrate S | 3.1 | cde | −28% |

As shown in Table 35, the foliar application of mixotrophic *Chlorella* based composition resulted in a significant difference from the UTC regarding shoot weight, showing an increase of 60% over the UTC in treatment 3. The soil application in treatment 3 also showed a 6% increase over the UTC. The Acadian product performed lower, showing only a 33% increase over the UTC in the foliar application, and showing a 28% decrease compared to the UTC in the soil application. These results show the small amounts of the mixotrophic *Chlorella* based composition at a low concentration and low frequency application are effective at improving shoot weight in plants when applied to the foliage.

With the characteristics that are shared among plants within the Solanaceae plant family, the results shown in the Examples are likely representative as to the effectiveness of a mixotrophic *Chlorella* based composition as described by throughout the specification on all plants in the Solanaceae plant family.

ASPECTS OF THE INVENTION

In one non-limiting embodiment, a method of enhancing yield of a Solanaceae plant may comprise: administering a liquid composition treatment comprising a *Chlorella* culture in which the microalgae cell content of the culture consists essentially of whole pasteurized cells in a concentration in the range of 0.001-0.400% solids by weight to a Solanaceae plant in an amount effective to increase utilization in a population of such plants compared to a substantially identical population of untreated plants.

In some embodiments, the administration may comprise contacting foliage of the plants with an effective amount of the liquid composition. In some embodiments, the liquid composition may comprise a concentration in the range of 0.003-0.080% solids by weight of whole pasteurized *Chlorella* cells.

In some embodiments, the liquid composition may be administered at a rate in the range of 10-50 gallons/acre. In some embodiments, the liquid composition may be administered by spraying. In some embodiments, the liquid composition may be administered every 3-28 days. In some embodiments, the liquid composition may be administered every 4-10 days. In some embodiments, the liquid composition may be first administered 5-14 days after the plant emerges from the soil.

In some embodiments, the administration may comprise contacting soil in the immediate vicinity of the plants with an effective amount of the liquid composition. In some embodiments, the liquid composition may comprise a concentration in the range of 0.003-0.055% solids by weight of whole pasteurized *Chlorella* cells. In some embodiments, the liquid composition may comprise a concentration in the range of 0.040-0.360% solids by weight of whole pasteurized *Chlorella* cells.

In some embodiments, the liquid composition may be administered at a rate in the range of 50-150 gallons per acre. In some embodiments, the liquid composition may be administered to the soil by a low volume irrigation system. In some embodiments, the liquid composition may be administered to the soil by a soil drench application. In some embodiments, the liquid composition may be administered every 3-28 days. In some embodiments, the liquid composition may be administered every 4-10 days. In some embodiments, the liquid composition may be first administered 5-14 days after the plant emerges from the soil.

In some embodiments, the Solanaceae plant may comprise at least one selected from the group consisting of tomato and bell pepper plants. In some embodiments, the whole *Chlorella* cells may not be subjected to a drying process. In some embodiments, the liquid composition may further comprise stabilizing means suitable for plants. In some embodiments, the *Chlorella* cells are cultured in mixotrophic conditions. In some embodiments, the liquid composition may not contain an active ingredient for enhancing a characteristic of the plant other than the culture of whole *Chlorella* cells.

In some embodiments, the method may further comprise increasing at least one selected from the group consisting of marketable plant weight, marketable plant yield, and marketable fruit weight. In some embodiments, the utilization may be increased by at least 80% compared to a substantially identical population of untreated plants. In some embodiments, the marketable plant weight may be increased by at least 200% compared to a substantially identical population of untreated plants. In some embodiments, the marketable plant yield may be increased by at least 150% compared to a substantially identical population of untreated plants. In some embodiments, the marketable fruit weight may be increased by at least 10% compared to a substantially identical population of untreated plants.

In another non-limiting embodiment, a method of enhancing yield of a Solanaceae plant may comprise: providing a liquid composition treatment comprising a *Chlorella* culture in which the microalgae cell content of the culture consists essentially of whole pasteurized *Chlorella* cells in a concentration in the range of 5-30% solids by weight; diluting the liquid composition with water to a concentration in the range of 0.001-0.400% solids by weight of whole pasteurized *Chlorella* cells; and administering the liquid composition treatment to a Solanaceae plant in an amount effective to increase plant yield in a population of such plants compared to a substantially identical population of untreated plants.

In another non-limiting embodiment, a method for enhancing yield of a Solanaceae plant may comprise: contacting soil in the immediate vicinity of a Solanaceae plant with a liquid composition treatment comprising a *Chlorella* culture in which the microalgae cell content of the culture consists essentially of whole pasteurized *Chlorella* cells in a concentration in the range of 0.001-0.400% solids by weight in an amount effective to increase production in a population of such plants compared to a substantially identical population of untreated plants.

In some embodiments, the method may further comprise increasing at least one from the group consisting of production plant weight and production fruit weight. In some embodiments, the production plant weight may be increased by at least 70% compared to a substantially identical population of untreated plants. In some embodiments, the production fruit weight may be increased by at least 70% compared to a substantially identical population of untreated plants.

In another non-limiting embodiment, a method for enhancing yield of a Solanaceae plant may comprise: contacting foliage of a Solanaceae plant with a liquid composition treatment comprising a *Chlorella* culture in which the microalgae cell content of the culture consists essentially of whole pasteurized cells in concentration in the range of 0.003-0.080% solids by weight in an amount effective to increase plant health in a population of such plants compared to a substantially identical population of untreated plants.

In some embodiments, the method may further comprise increasing at least one from the group consisting of chlorophyll content, whole plant weight, root weight, and shoot weight. In some embodiments, the chlorophyll content may be increased by at least 20% compared to a substantially identical population of untreated plants. In some embodiments, the whole plant weight may be increased by at least 50% compared to a substantially identical population of untreated plants. In some embodiments, the root weight may be increased by at least 50% compared to a substantially identical population of untreated plants. In some embodiments, the shoot weight is increased by at least 50% compared a substantially identical population of untreated plants.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

What is claimed is:

1. A method for enhancing yield of a Solanaceae plant, the method comprising: administering a liquid composition treatment comprising a *Chlorella* culture in which the microalgae cell content of the culture consists essentially of whole pasteurized *Chlorella* cells in a concentration in the range of 0.001-0.400% solids by weight to a Solanaceae plant in an amount effective to increase utilization in a population of such plants compared to a substantially identical population of untreated plants.

2. The method of claim 1, wherein the administration comprises contacting foliage of the plants with an effective amount of the liquid composition.

3. The method of claim 2, wherein the liquid composition comprises a concentration in the range of 0.003-0.080% solids by weight of whole pasteurized *Chlorella* cells.

4. The method of claim 3, wherein the liquid composition is administered at a rate in the range of 10-50 gallons/acre.

5. The method of claim 2, wherein the liquid compositions is administered by spraying.

6. The method of claim 2, wherein the liquid composition is administered every 3-28 days.

7. The method of claim 6, wherein the liquid composition is administered every 4-10 days.

8. The method of claim 2, wherein the liquid composition is first administered 5-14 days after the plants emerges from the soil.

9. The method of claim 1, wherein the administration comprises contacting soil in the immediate vicinity of the plants with an effective amount of the liquid composition.

10. The method of claim 9, wherein the liquid composition comprises a concentration in the range of 0.003-0.055% solids by weight of whole pasteurized *Chlorella* cells.

11. The method of claim 9, wherein the liquid composition comprises a concentration in the range of 0.040-0.360% solids by weight of whole pasteurized *Chlorella* cells.

12. The method of claim 9, wherein the liquid composition is administered at a rate in the range of 50-150 gallons per acre.

13. The method of claim 9, wherein the liquid composition is administered to the soil by a low volume irrigation system.

14. The method of claim 9, wherein the liquid composition is administered to the soil by a soil drench application.

15. The method of claim 9, wherein the liquid composition is administered every 3-28 days.

16. The method of claim 15, wherein the liquid composition is administered every 4-10 days.

17. The method of claim 9, wherein the liquid composition is first administered 5-14 days after the plant emerges from the soil.

18. The method of claim 1, wherein the Solanaceae plant comprises at least one selected from the group consisting of tomato and bell pepper plants.

19. The method of claim 1, wherein the whole *Chlorella* cells have not been subjected to a drying process.

20. The method of claim 1, wherein the liquid composition further comprises at least one selected from the group consisting of phosphoric acid and potassium sorbate.

21. The method of claim 1, wherein the *Chlorella* cells are cultured in mixotrophic conditions.

22. The method of claim 1, wherein the liquid composition does not contain an active ingredient for increasing utilization in the population of plants other than the culture of whole *Chlorella* cells.

23. The method of claim 1, wherein the method further comprises increasing at least one from the group consisting of marketable plant weight, marketable plant yield, and marketable fruit weight.

24. The method of claim 1, wherein the utilization is increased by at least 80% compared to a substantially identical population of untreated plants.

25. The method of claim 23, wherein the marketable plant weight is increased by at least 200% compared to a substantially identical population of untreated plants.

26. The method of claim 23, wherein the marketable plant yield is increased by at least 150% compared to a substantially identical population of untreated plants.

27. The method of claim 23, wherein the marketable fruit weight is increased by at least 10% compared to a substantially identical population of untreated plants.

28. A method of enhancing yield of a Solanaceae plant, the method comprising:
   a. Providing a liquid composition treatment comprising a *Chlorella* culture in which the microalgae cell content of the culture consists essentially of whole pasteurized *Chlorella* cells in a concentration in the range of 5-30% solids by weight;
   b. Diluting the liquid composition with water to a concentration in the range of 0.001-0.400% solids by weight of whole pasteurized *Chlorella* cells; and
   c. Administering the liquid composition treatment to a Solanaceae plant in an amount effective to increase plant yield in a population of such plants compared to a substantially identical population of untreated plants.

29. The method of claim 28, wherein the liquid composition is administered to at least one of soil in the immediate vicinity of the plants and foliage of the plants.

30. The method of claim 28, wherein the liquid composition is administered every 3-28 days.

* * * * *